(12) United States Patent
Takahashi et al.

(10) Patent No.: US 11,060,134 B2
(45) Date of Patent: Jul. 13, 2021

(54) CELL SELECTION METHOD, CELL DETECTION METHOD, CELL SELECTION APPARATUS, AND CELL DETECTION APPARATUS

(71) Applicant: Sysmex Corporation, Kobe (JP)

(72) Inventors: Yusuke Takahashi, Kobe (JP); Masatoshi Yanagida, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 9 days.

(21) Appl. No.: 15/363,503

(22) Filed: Nov. 29, 2016

(65) Prior Publication Data

US 2017/0152552 A1    Jun. 1, 2017

(30) Foreign Application Priority Data

Nov. 30, 2015  (JP) .............................. JP2015-234215

(51) Int. Cl.
*G01N 33/00*   (2006.01)
*C12Q 1/6841*  (2018.01)
*G01N 21/64*   (2006.01)

(52) U.S. Cl.
CPC ....... *C12Q 1/6841* (2013.01); *G01N 21/6428* (2013.01); *G01N 2021/6439* (2013.01)

(58) Field of Classification Search
None
See application file for complete search history.

(56) References Cited

U.S. PATENT DOCUMENTS

| | | | | |
|---|---|---|---|---|
| 5,200,313 A * | 4/1993 | Carrico | ................... | C12Q 1/68 435/6.11 |
| 5,437,980 A * | 8/1995 | Haugland | ................ | C09B 15/00 435/6.12 |
| 5,545,521 A | 8/1996 | Okamoto et al. | | |
| 6,060,240 A * | 5/2000 | Kamb | ................ | C12N 15/1065 435/320.1 |
| 6,211,955 B1 | 4/2001 | Basiji et al. | | |
| 6,355,435 B1 * | 3/2002 | Wilson | ................... | C07H 21/00 435/6.11 |
| 8,548,219 B2 | 10/2013 | Ortyn et al. | | |
| 2002/0065609 A1 * | 5/2002 | Ashby | ................... | C12Q 1/683 702/20 |
| 2002/0119455 A1 * | 8/2002 | Chan | ................... | C12Q 1/6869 435/6.12 |
| 2003/0157512 A1 * | 8/2003 | Bermingham, Jr. | ......................... | C07K 14/705 435/6.16 |
| 2004/0067581 A1 * | 4/2004 | Izbicki | ................. | C12N 5/0693 435/366 |
| 2005/0079531 A1 | 4/2005 | Coignet | | |
| 2006/0246481 A1 | 11/2006 | Finch et al. | | |
| 2006/0286570 A1 * | 12/2006 | Rowlen | ................ | C12Q 1/6816 435/6.12 |
| 2007/0009954 A1 * | 1/2007 | Wang | ................... | C12Q 1/6823 435/6.12 |
| 2007/0031829 A1 * | 2/2007 | Yasuno | ................ | C12Q 1/6886 435/6.12 |
| 2007/0042419 A1 * | 2/2007 | Barany | ................ | C12Q 1/6851 435/6.12 |
| 2007/0109530 A1 | 5/2007 | Ueno et al. | | |
| 2007/0161008 A1 | 7/2007 | Morrison et al. | | |
| 2008/0213783 A1 * | 9/2008 | Hainfeld | ............. | C12N 9/0065 435/6.12 |
| 2009/0258350 A1 | 10/2009 | Morrison et al. | | |
| 2010/0285077 A1 * | 11/2010 | Lintner | .................. | A61Q 19/08 424/401 |
| 2010/0323345 A1 * | 12/2010 | Borisy | ................. | C12Q 1/6841 435/5 |
| 2011/0039258 A1 * | 2/2011 | McNeeley | ........... | C12N 5/0634 435/6.12 |
| 2012/0082978 A1 * | 4/2012 | Pilarski | ................ | C12Q 1/6841 435/6.11 |
| 2012/0115146 A1 | 5/2012 | Mishima et al. | | |
| 2012/0165219 A1 * | 6/2012 | Van Der Zaag | ..... | C12Q 1/6834 506/9 |
| 2012/0200694 A1 | 8/2012 | Garsha et al. | | |
| 2012/0282601 A1 | 11/2012 | Abe et al. | | |
| 2013/0225623 A1 * | 8/2013 | Buxbaum | ............ | A61K 31/198 514/277 |
| 2013/0287755 A1 * | 10/2013 | Greene | ................... | A61P 37/02 424/94.5 |
| 2014/0335606 A1 * | 11/2014 | Yoon | .................... | C12Q 1/6881 435/325 |

(Continued)

FOREIGN PATENT DOCUMENTS

CN    1967244 A      5/2007
CN    102741425 A    10/2012
(Continued)

OTHER PUBLICATIONS

"How many species of bacteria are there" (wisegeek.com; accessed Jan. 21, 2014). (Year: 2014).*

(Continued)

*Primary Examiner* — Bradley L. Sisson
(74) *Attorney, Agent, or Firm* — Brinks Gilson & Lione

(57) ABSTRACT

Disclosed is a cell selection method including a sample preparation step of preparing a sample by performing staining of nucleic acid in each of cells by a first fluorescent dye; and hybridization with respect to an evaluation target region in DNA in each cell by an evaluation probe including a second fluorescent dye; a light receiving step of applying light to the sample and receiving fluorescence from the first fluorescent dye and fluorescence from the second fluorescent dye; and a selection step of selecting an analysis target cell on the basis of intensity of the fluorescence from the first fluorescent dye and intensity of the fluorescence from the second fluorescent dye, wherein the first fluorescent dye is a dye that emits fluorescence having a first wavelength, and the second fluorescent dye is a dye that emits fluorescence having a second wavelength different from the first wavelength.

14 Claims, 20 Drawing Sheets

(56) References Cited

U.S. PATENT DOCUMENTS

| | | | |
|---|---|---|---|
| 2015/0045396 A1* | 2/2015 | Takeuchi | A61K 31/4439 514/342 |
| 2015/0316535 A1* | 11/2015 | Hare | A61P 9/06 424/130.1 |
| 2017/0029878 A1 | 2/2017 | Isoda et al. | |

FOREIGN PATENT DOCUMENTS

| | | |
|---|---|---|
| CN | 102768179 A | 11/2012 |
| EP | 3121292 A1 | 1/2017 |
| JP | H6-178699 A | 6/1994 |
| JP | 2008-535482 A | 9/2008 |
| JP | 2011-517573 A | 6/2011 |
| JP | 2012-103077 A | 5/2012 |
| JP | 2013-507612 A | 3/2013 |
| WO | WO 03/048300 A2 | 6/2003 |
| WO | WO 2006/098978 A1 | 9/2006 |
| WO | WO 2007/133710 A2 | 11/2007 |
| WO | WO 2009/129154 A1 | 10/2009 |
| WO | 2015/141856 A1 | 9/2015 |

OTHER PUBLICATIONS

"Fungi," (Wikipedia.com; accessed Jun. 3, 2013). (Year: 2013).*
"Plant," (Wikipedia.com; accessed Aug. 28, 2015). (Year: 2015).*
"Mammal," (Wikipedia.com; accessed Sep. 22, 2011). (Year: 2011).*
"Murinae," (Wikipedia.com, accessed Mar. 18, 2013). (Year: 2013).*
"Fish," (Wikipedia.com, accessed Nov. 2, 2014). (Year: 2014).*
"Algae," Wikipedia.com (accessed Mar. 4, 2016). (Year: 2016).*
"Protozoa," Wikipedia.com (accessed May 11, 2016). (Year: 2016).*
"List of sequenced bacterial genomes" (Wikipedia.com; accessed Jan. 24, 2014). (Year: 2014).*
Forster et al., "A human gut bacterial genome and culture collection for improved metagenomic analyses", Nature Biotechnology, vol. 37, Feb. 2019, 186-192. (Year: 2019).*
Sah et al., "Complete Genome Sequence of a 2019 Novel Coronavirus (SARS-CoV-2) Strain Isolated in Nepal", Microbiology Resource Announcements, vol. 9, Issue 11, Mar. 12, 2020. (Year: 2020).*
Zeberg and Paabo, "The major genetic risk factor for severe COVID-19 is inherited from Neanderthals", Nature, Sep. 30, 2020. (Year: 2020).*
Dolgova and Lao, "Evolutionary and Medical Consequences of Archaic Introgression into Modern Human Genomes", Genes, 9, 358, Jul. 18, 2018. (Year: 2018).*
Anonymous, "BD FACSCalibur Flow Cytometer", BD Sciences, Jun. 2002, pp. 1-9.
Bozzetti, C. et al., "HER-2/neu Amplification Detected by Fluorescence in Situ Hybridization in Fine Needle Aspirates From Primary Breast Cancer", Annals of Oncology, vol. 13, No. 9, Sep. 1, 2002, pp. 1398-1403.
Brouzes, E. et al., "Droplet Microfluidic Technology for Single-Cell Hight-Throughput Screening", Proceedings National Academy of Sciences, PNAS, National Academy of Sciences, vol. 106, No. 34, Aug. 25, 2009, pp. 14195-14200.
Kao et al., "A Fluorescence in Situ Hybridization (FISH) Microfluidic Platform for Detection of HER2 Amplification in Cancer Cells", Biosensors and Bioelectronics, vol. 69, Jul. 15, 2015, pp. 272-279.
Lopez, C. et al., "Is It Necessary to Evaluate Nuclei in HER2 FISH Evaluation?", American Journal of Clinical Pathology, vol. 139, No. 1, Dec. 27, 2012, pp. 47-54.
Siu, L. et al, "Application of Tri-Colour, Dual Fusion Fluorescence in Situ Hybridization (FISH) System for the Characterization of BCR-ABL1 Fusion in Chronic Myelogenous Leukemia (CML) and Residual Disease Monitoring", BMC Blood Disorders, vol. 9, No. 1, Jul. 7, 2009, pp. 4.
Japanese Office Action dated Aug. 27, 2019 in a counterpart Japanese patent application No. 2015-234215.
Wangron Wen et al: Clinical Molecular Diagnostics, Guangdong Science Technology Press, Mar. 2014, p. 90, ISBN 978-7-5359-6311-6.
Zhiying Ji et al: "Chromosomics: Detection of Numerical and Structural Alterations in All 24 Human Chromosomes Simultaneously Using a Novel OctoChrome FISH Assay", JoVE-Journal of Visualized Experiments, Feb. 6, 2012, 60: e3619, pp. 1-7.
Jun Lu et al: "Research progress of fluorescence in situ hybridization technique and its future in chromosome identification applications", Journal of Anhui Agricultural Sciences, 2008, vol. 36, No. 3, pp. 911-913.
Chinese Office Action dated Jun. 19, 2020 in a counterpart Chinese patent application No. 201611016107.0.
Chinese Office Action dated May 7, 2021 in a counterpart Chinese patent application No. 201611016107.0.

* cited by examiner

FIG. 6
| | BRIGHT FIELD | Ch17 | NUCLEUS | Her2 |
|---|---|---|---|---|
| REGION 102 | 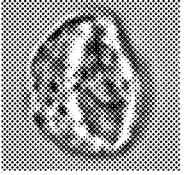 | 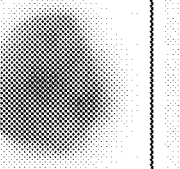 | 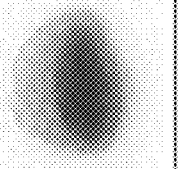 | 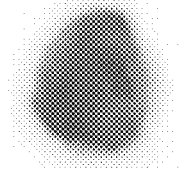 |
| REGION 101 | 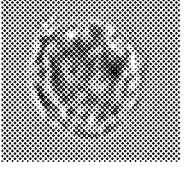 | 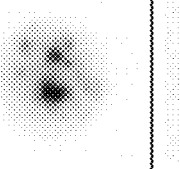 | 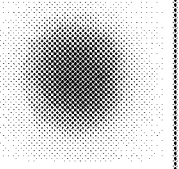 | 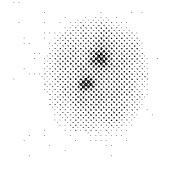 |
| REGION 101 | 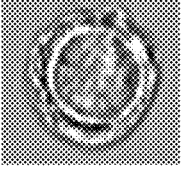 | 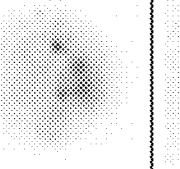 | 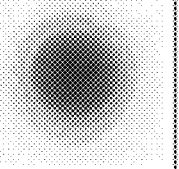 | 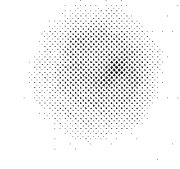 |
| REGION 103 | | | | |
| REGION 103 | | | | |

FIG. 7A CONTROL CELL
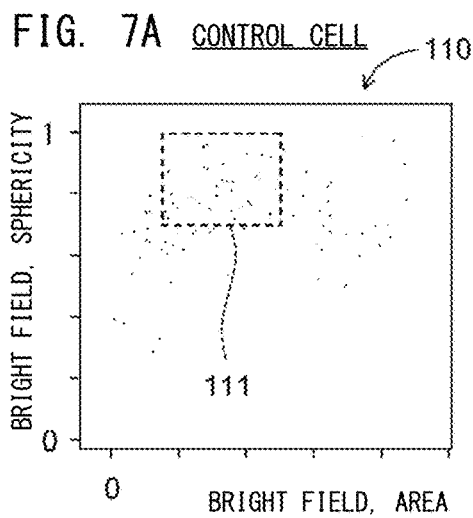
FIG. 7B ABNORMAL CELL
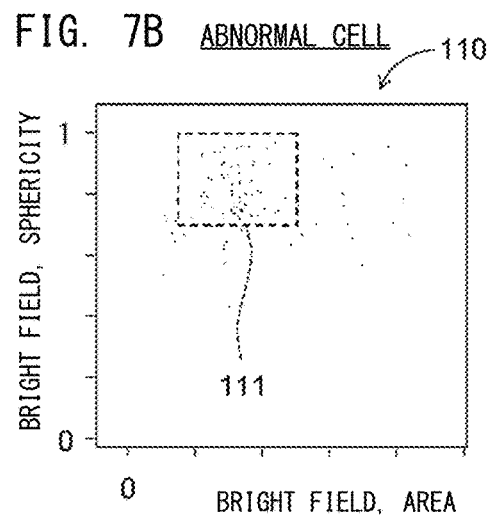
FIG. 7C CONTROL CELL
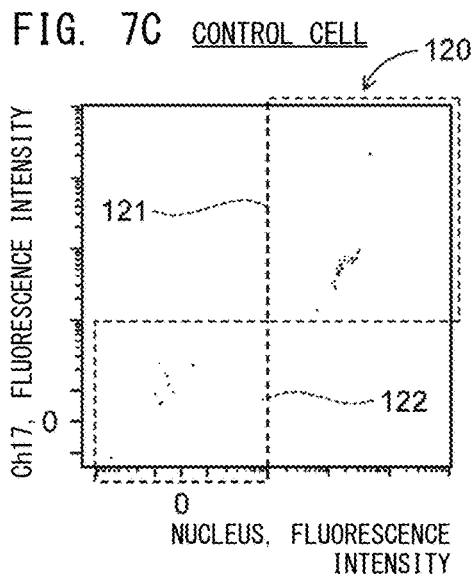
FIG. 7D ABNORMAL CELL
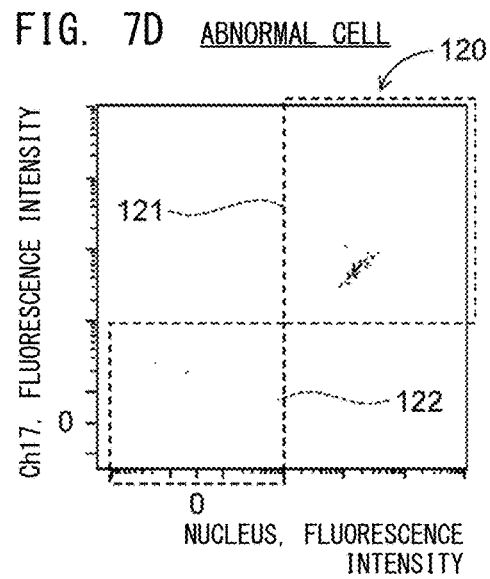
FIG. 7E CONTROL CELL
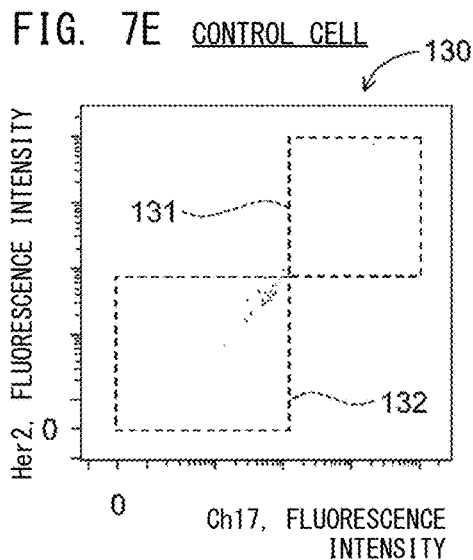
FIG. 7F ABNORMAL CELL
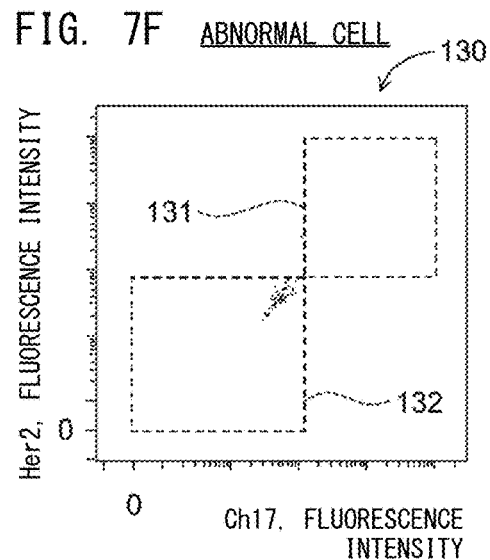

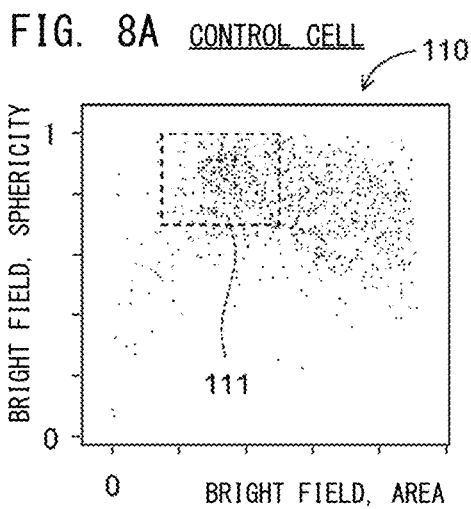
FIG. 8A CONTROL CELL
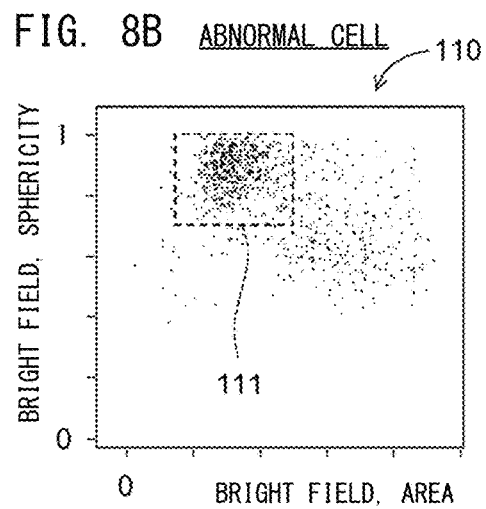
FIG. 8B ABNORMAL CELL
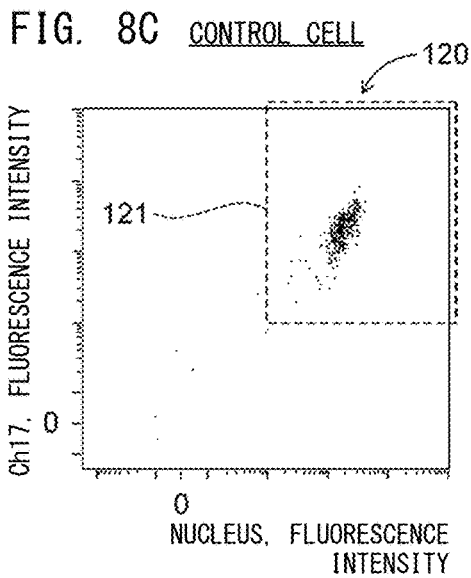
FIG. 8C CONTROL CELL
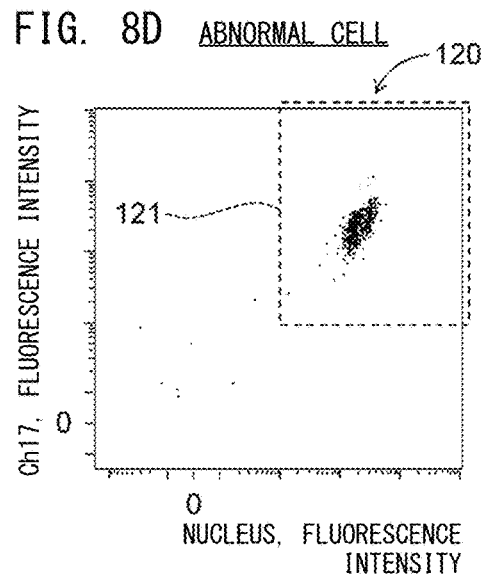
FIG. 8D ABNORMAL CELL
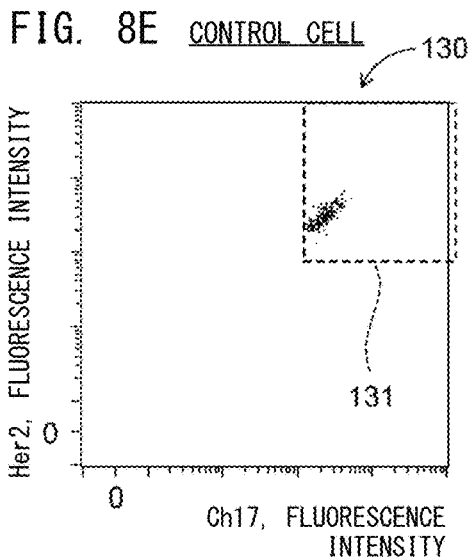
FIG. 8E CONTROL CELL
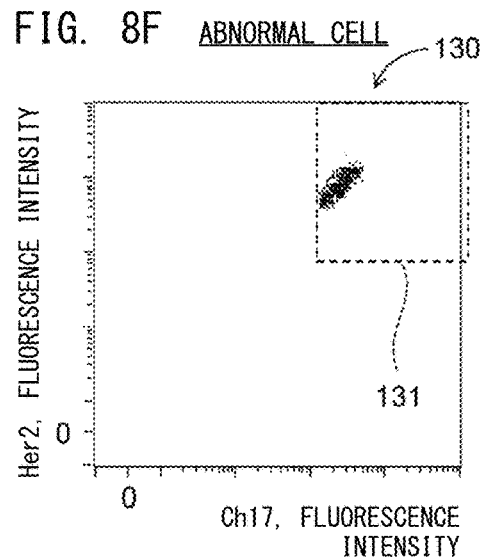
FIG. 8F ABNORMAL CELL

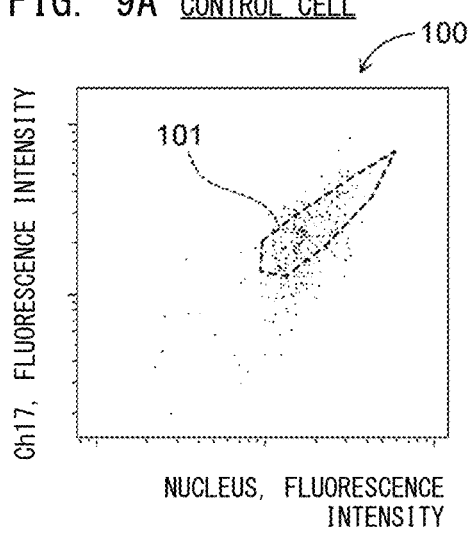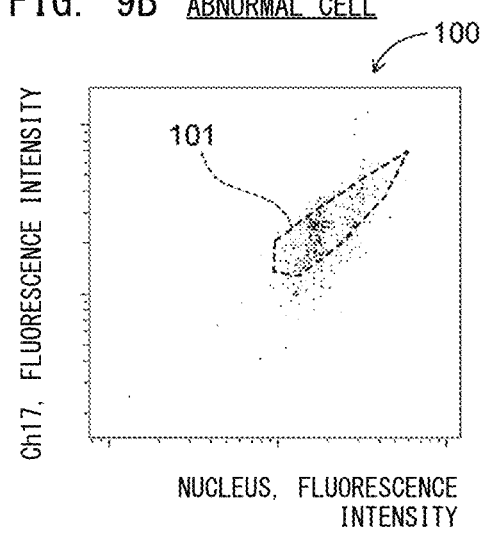
FIG. 9A CONTROL CELL
FIG. 9B ABNORMAL CELL

NORMAL CELL,
TRANSLOCATION NEGATIVE

ABNORMAL CELL,
TRANSLOCATION POSITIVE

NORMAL CELL,
TRANSLOCATION NEGATIVE

ABNORMAL CELL,
TRANSLOCATION POSITIVE

NORMAL CELL.
TRANSLOCATION NEGATIVE

ABNORMAL CELL.
TRANSLOCATION POSITIVE

NORMAL CELL.
TRANSLOCATION NEGATIVE

ABNORMAL CELL.
TRANSLOCATION POSITIVE

FIG. 13

| DETECTION TARGET |
| --- |
| ALK TRANSLOCATION |
| AML1-ETO TRANSLOCATION |
| RUNX1-RUNX1T1 TRANSLOCATION |
| APL2-MALT1 TRANSLOCATION |
| ATM DEL(11) LONG ARM DELETION |
| BCL6 3Q27 TRANSLOCATION |
| BCR-ABL TRANSLOCATION |
| CBFβ INV(16) INVERSION |
| CSF1 RECEPTOR DEL(5) LONG ARM DELETION |
| D13S319 DEL(13) LONG ARM DELETION |
| D7S486 DEL(7) LONG ARM DELETION |
| DEL(20) LONG ARM DELETION |
| EGFR DEL(5) LONG ARM DELETION |
| FGFR1 8P12 TRANSLOCATION |
| FIP1L1-PDGFRα DEL(4) LONG ARM DELETION |
| IGH/C-MYC TRANSLOCATION |
| IGH-BCL1 TRANSLOCATION |
| IGH-BCL2 TRANSLOCATION |
| IGH-FGFR3 TRANSLOCATION |
| IGH-MAF TRANSLOCATION |
| MLL TRANSLOCATION |
| MYC TRANSLOCATION |
| NUP98 TRANSLOCATION |
| P53 DEL(17) SHORT ARM DELETION |
| PDGFRβ TRANSLOCATION |
| PML-RARA TRANSLOCATION |
| TCF3/PBX1 TRANSLOCATION |
| TEL-AML1 TRANSLOCATION |
| CBFB-MYH11 TRANSLOCATION |
| MLLT3-MLL TRANSLOCATION |
| DEK-NUP214 TRANSLOCATION |
| RPN1-EV1 TRANSLOCATION |
| RBM15-MKL1 TRANSLOCATION |
| IL3-IGH TRANSLOCATION |
| HER2 AMPLIFICATION |

CELL SELECTION METHOD, CELL DETECTION METHOD, CELL SELECTION APPARATUS, AND CELL DETECTION APPARATUS

RELATED APPLICATIONS

This application claims priority from prior Japanese Patent Application No. 2015-234215, filed on Nov. 30, 2015, entitled "CELL SELECTION METHOD, CELL DETECTION METHOD, CELL SELECTION APPARATUS, AND CELL DETECTION APPARATUS", the entire content of which is incorporated herein by reference.

BACKGROUND OF THE INVENTION

1. Field of the Invention

The present invention relates to cell selection methods, cell detection methods, cell selection apparatuses, and cell detection apparatuses.

2. Description of the Related Art

International Publication No. WO03/048300 describes a cell processing method to be used when a flow cytometer or the like is applied to detection of a fluorescence in situ hybridization (FISH). According to FISH, abnormal cells can be detected by causing a labeled probe to be bound to a DNA sequence region being the detection target in each cell, thereby staining the cell, and then, by detecting fluorescence caused by the labeled probe.

SUMMARY OF THE INVENTION

The scope of the present invention is defined solely by the appended claims, and is not affected to any degree by the statements within this summary.

When in situ hybridization is performed, cells poorly stained by a labeled probe and cells having nonspecifically reacted appear in some cases. When such poorly stained cells are mixed in analysis target cells, abnormal cells cannot be accurately detected as a result. Thus, a method that allows accurate detection of abnormal cells has been desired.

A first mode of the present invention relates to a cell selection method. The cell selection method according to the present mode includes a sample preparation step of preparing a sample by performing staining of nucleic acid in each of cells by a first fluorescent dye; and hybridization with respect to an evaluation target region in DNA in each cell by an evaluation probe including a second fluorescent dye; a light receiving step of applying light to the sample and receiving fluorescence from the first fluorescent dye and fluorescence from the second fluorescent dye; and a selection step of selecting an analysis target cell on the basis of intensity of the fluorescence from the first fluorescent dye and intensity of the fluorescence from the second fluorescent dye. The first fluorescent dye is a dye that emits fluorescence having a first wavelength, and the second fluorescent dye is a dye that emits fluorescence having a second wavelength different from the first wavelength.

A second mode of the present invention relates to a cell selection method. The cell selection method according to the present mode includes a sample preparation step of preparing a sample by performing staining of nucleic acid in each of cells by a first fluorescent dye; and hybridization with respect to an evaluation target region in DNA in each cell by an evaluation probe including a second fluorescent dye; an image capturing step of applying light to the sample and capturing an image of the cell in the sample; a brightness obtaining step of obtaining, on the basis of the image of the cell captured in the image capturing step, brightness of an image of fluorescence from the first fluorescent dye and brightness of an image of fluorescence from the second fluorescent dye; and a selection step of selecting an analysis target cell on the basis of the brightness of the image of the fluorescence from the first fluorescent dye and the brightness of the image of the fluorescence from the second fluorescent dye. The first fluorescent dye is a dye that emits fluorescence having a first wavelength, and the second fluorescent dye is a dye that emits fluorescence having a second wavelength different from the first wavelength.

A third mode of the present invention relates to a cell detection method. The cell detection method according to the present mode includes a sample preparation step of preparing a sample by performing staining of nucleic acid in each of cells by a first fluorescent dye; hybridization with respect to an evaluation target region in DNA in each cell by an evaluation probe including a second fluorescent dye; and hybridization with respect to a detection target region in DNA in the cell by a detection probe including a third fluorescent dye; a light receiving step of applying light to the sample and receiving fluorescence from the first fluorescent dye, fluorescence from the second fluorescent dye, and fluorescence from the third fluorescent dye; a selection step of selecting an analysis target cell on the basis of intensity of the fluorescence from the first fluorescent dye and intensity of the fluorescence from the second fluorescent dye; and a detection step of detecting an abnormal cell from the analysis target cell on the basis of the fluorescence from the third fluorescent dye. The first fluorescent dye is a dye that emits fluorescence having a first wavelength, the second fluorescent dye is a dye that emits fluorescence having a second wavelength different from the first wavelength, and the third fluorescent dye is a dye that emits fluorescence having a third wavelength different from the first and second wavelengths.

A fourth mode of the present invention relates to a cell selection apparatus. The cell selection apparatus according to the present mode includes a sample preparation unit configured to prepare a sample by mixing cells, a nucleic acid staining reagent that includes a first fluorescent dye for staining nucleic acid in each cell, and a reagent that includes an evaluation probe including a second fluorescent dye and configured to be hybridized to an evaluation target region in DNA in the cell; a flow cell configured to allow the sample to flow therein; a light source configured to apply light to the sample flowing in the flow cell; a light receiving unit configured to receive fluorescence from the first fluorescent dye and fluorescence from the second fluorescent dye; and a processing unit. The first fluorescent dye is a dye that emits fluorescence having a first wavelength, and the second fluorescent dye is a dye that emits fluorescence having a second wavelength different from the first wavelength. The processing unit selects an analysis target cell on the basis of intensity of the fluorescence from the first fluorescent dye and intensity of the fluorescence from the second fluorescent dye.

A fifth mode of the present invention relates to a cell selection apparatus. The cell selection apparatus according to the present mode includes a sample preparation unit configured to prepare a sample by mixing cells, a nucleic acid staining reagent that includes a first fluorescent dye for staining nucleic acid in each cell, and a reagent that includes an evaluation probe including a second fluorescent dye and configured to be hybridized to an evaluation target region in DNA in the cell; a flow cell configured to allow the sample to flow therein; a light source configured to apply light to the sample flowing in the flow cell; an image capturing unit configured to capture an image of the cell in the sample; and a processing unit. The first fluorescent dye is a dye that emits fluorescence having a first wavelength, and the second fluorescent dye is a dye that emits fluorescence having a second wavelength different from the first wavelength. The processing unit obtains, on the basis of the image of the cell captured by the image capturing unit, brightness of an image of the fluorescence from the first fluorescent dye, and brightness of an image of the fluorescence from the second fluorescent dye, and selects an analysis target cell on the basis of the brightness of the image of the fluorescence from the first fluorescent dye and the brightness of the image of the fluorescence from the second fluorescent dye.

A sixth mode of the present invention relates to a cell detection apparatus. The cell detection apparatus according to the present mode includes a sample preparation unit configured to prepare a sample by mixing cells, a nucleic acid staining reagent that includes a first fluorescent dye for staining nucleic acid in each cell, a reagent that includes an evaluation probe including a second fluorescent dye and configured to be hybridized to an evaluation target region in DNA in the cell, and a reagent that includes a detection probe including a third fluorescent dye and configured to be hybridized to a detection target region in DNA in the cell; a flow cell configured to allow the sample to flow therein; a light source configured to apply light to the sample flowing in the flow cell; a light receiving unit configured to receive fluorescence from the first fluorescent dye, fluorescence from the second fluorescent dye, and fluorescence from the third fluorescent dye; and a processing unit. The first fluorescent dye is a dye that emits fluorescence having a first wavelength, the second fluorescent dye is a dye that emits fluorescence having a second wavelength different from the first wavelength, and the third fluorescent dye is a dye that emits fluorescence having a third wavelength different from the first and second wavelengths. The processing unit selects an analysis target cell on the basis of intensity of the fluorescence from the first fluorescent dye and intensity of the fluorescence from the second fluorescent dye, and detects an abnormal cell from the analysis target cell on the basis of the fluorescence from the third fluorescent dye.

BRIEF DESCRIPTION OF THE DRAWINGS

FIG. 6 shows examples of bright field images and fluorescence images obtained from cells in three different regions in the scattergram for selecting analysis target cells according to Embodiment 1.

FIG. 7A shows a scattergram and a region created in order to remove unnecessary particles in verification according to Embodiment 1.

FIG. 7B shows a scattergram and a region created in order to remove unnecessary particles in verification according to Embodiment 1.

FIG. 7C shows a scattergram and regions created in order to remove unnecessary particles in verification according to Embodiment 1.

FIG. 7D shows a scattergram and regions created in order to remove unnecessary particles in verification according to Embodiment 1.

FIG. 7E shows a scattergram and regions created in order to remove unnecessary particles in verification according to Embodiment 1.

FIG. 7F shows a scattergram and regions created in order to remove unnecessary particles in verification according to Embodiment 1.

FIG. 8A shows a scattergram created in verification according to Embodiment 1, and a region for narrowing-down analysis target cells set in the scattergram.

FIG. 8B shows a scattergram created in verification according to Embodiment 1, and a region for narrowing-down analysis target cells set in the scattergram.

FIG. 8C shows a scattergram created in verification according to Embodiment 1, and a region for narrowing-down analysis target cells set in the scattergram.

FIG. 8D shows a scattergram created in verification according to Embodiment 1, and a region for narrowing-down analysis target cells set in the scattergram.

FIG. 8E shows a scattergram created in verification according to Embodiment 1, and a region for narrowing-down analysis target cells set in the scattergram.

FIG. 8F shows a scattergram created in verification according to Embodiment 1, and a region for narrowing-down analysis target cells set in the scattergram.

FIG. 9A shows a scattergram and a region for selecting analysis target cells in verification according to Embodiment 1.

FIG. 9B shows a scattergram and a region for selecting analysis target cells in verification according to Embodiment 1.

FIG. 13 is a diagram explaining that abnormal cells can be detected by determining various genomic abnormalities according to Embodiments 1 to 4.

DETAILED DESCRIPTION OF THE PREFERRED EMBODIMENTS

Figure 1:
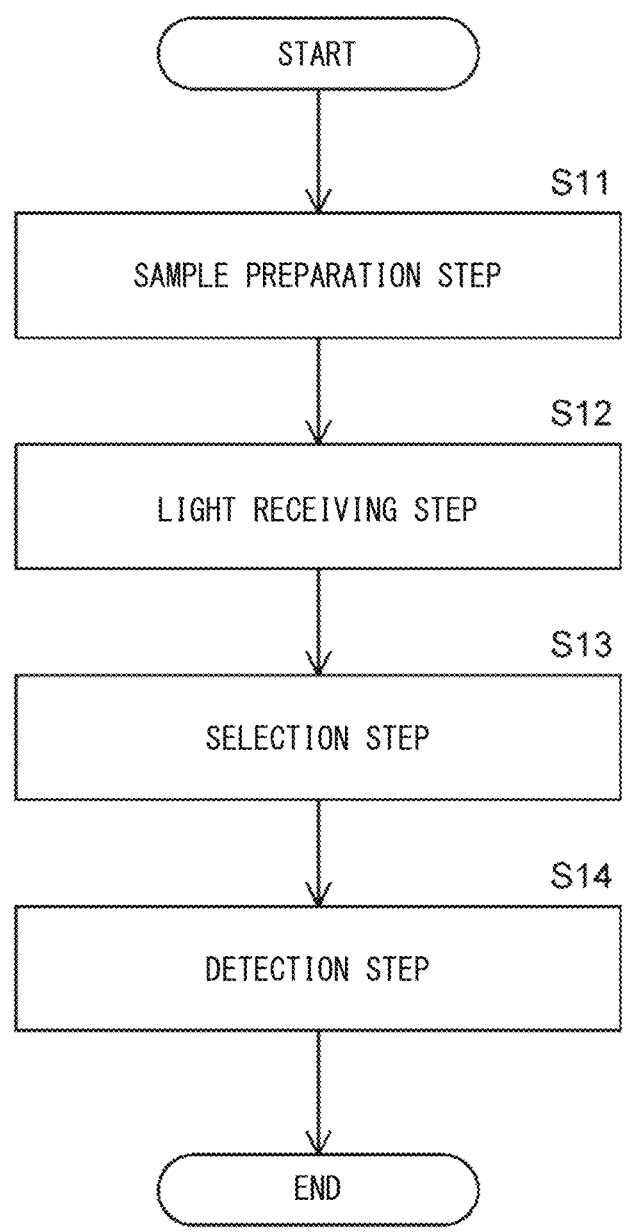
FIG. 1 is a flow chart showing a cell detection method according to Embodiment 1.

The present invention provides a selection method for excluding, from the analysis target, cells poorly stained by a labeled probe and cells in which nonspecific binding of the labeled probe has occurred; and selecting, as the analysis target, cells in which appropriate hybridization of the labeled probe to a DNA sequence region being the detection target has occurred. The present invention also provides a detection method for detecting, from the selected cells, abnormal cells in which genomic abnormality has occurred.

Herein, "genomic abnormality" means that a sequence different from the wild-type DNA sequence is generated. "Genomic abnormality" includes gene amplification, deletion, inversion, translocation, and the like, for example.

"Gene amplification" means that a specific gene in the genome is amplified. "Deletion" means that a part of a chromosome, for example, the long arm or the short arm, is lost. "Translocation" means that a part of a chromosome is cut and attached/fused to another chromosome. "Inversion" means that the order of DNA base sequence on a chromosome is partially inversed.

"Gene" includes, for example, expression regulatory regions, coding regions, and exons or introns, irrespective of functional domains. Thus, the term "gene" includes regulatory sequences such as promoter, enhancer, and termination signal, in addition to coding region. Regulatory sequences of a gene may be located proximal to, in, or distal to a coding region.

"Abnormal cell" is a cell in which at least one of genomic abnormalities of gene amplification, deletion, inversion, and translocation has occurred. "Normal cell" is a cell in which none of gene amplification, deletion, inversion, and translocation has occurred.

"Detection probe" includes a polynucleotide complementary to the base sequence of the detection target region in DNA in a cell; and a fluorescence substance which labels the polynucleotide. The fluorescence substance may directly or indirectly bind to the polynucleotide. Here, "indirectly bind" means that the fluorescence substance binds to the polynucleotide via another substance (hereinafter, mediator) such as an antibody. As the mediator, a hapten, an anti-hapten antibody, and the like can be used. For example, a hapten that binds to the polynucleotide, an anti-hapten primary antibody, and a labeled secondary antibody that binds to the primary antibody can be used. Without using a secondary antibody, a labeled anti-hapten primary antibody may be used. Herein, when a mediator is used, the complex of the polynucleotide, the mediator, and the fluorescence substance will be collectively referred to as a "detection probe". Examples of the hapten include biotin, desthiobiotin and other derivatives thereof, dinitrophenol (DNP), and digoxigenin (DIG). As the anti-hapten primary antibody, an anti-DNP antibody or an anti-DIG antibody can be used, for example. A scavenger which binds to biotin can be avidin, streptavidin, or an antibody. An antibody can be used as a scavenger for other haptens. The secondary antibody may be any secondary antibody as long as it can bind to the primary antibody, and is a goat-derived anti-rabbit antibody or a goat-derived anti-mouse antibody, for example.

"Evaluation probe" includes a polynucleotide complementary to the base sequence of the evaluation target region in DNA in a cell; and a fluorescence substance which labels the polynucleotide. The fluorescence substance may directly or indirectly bind to the polynucleotide. Here, "indirectly bind" has the same meaning as that described above. Herein, when a mediator is used, the complex of the polynucleotide, the mediator, and the fluorescence substance will be collectively referred to as an "evaluation probe". A hapten, an anti-hapten primary antibody, and a secondary antibody are the same as described above.

When the detection probe includes a mediator, the mediator needs to be a substance that specifically binds to the polynucleotide of the detection probe, and that substantially does not bind to the polynucleotide of the evaluation probe. Similarly, when the evaluation probe includes a mediator, this mediator needs to be a substance that specifically binds to the polynucleotide of the evaluation probe, and that substantially does not bind to the polynucleotide of the detection probe.

When each of the detection probe and the evaluation probe includes a labeled antibody that specifically binds to a hapten, the haptens that bind to the polynucleotides need to be substances that are different from each other, between the detection probe and the evaluation probe. For example, when DNP is used as the hapten that binds to the polynucleotide of the detection probe, DIG needs to be used as the hapten that binds to the polynucleotide of the evaluation probe.

When each of the detection probe and the evaluation probe includes a labeled secondary antibody that binds to a primary antibody, the labeled secondary antibody included in the detection probe needs to be a substance that specifically binds to the primary antibody for the detection probe, and that substantially does not bind to the primary antibody for the evaluation probe. Similarly, the labeled secondary antibody included in the evaluation probe needs to be a substance that specifically binds to the primary antibody for the evaluation probe and that substantially does not bind to the primary antibody for the detection probe. For example, the primary antibody for the detection probe and the primary antibody for the evaluation probe are created from different animal species, respectively, and antibodies for the respective antibodies of the specific animal species can be used as the secondary antibodies. For example, for the detection probe, a mouse antibody can be used as the primary antibody and an anti-mouse antibody can be used as the secondary antibody; and for the evaluation probe, a rabbit antibody can be used as the primary antibody and an anti-rabbit antibody can be used as the secondary antibody. When labeled secondary antibodies are used, it is further preferable that, between the detection probe and the evaluation probe, the binding modes between the primary antibody and the hapten bound to the polynucleotide are different.

As the fluorescence substances respectively included in the detection probe and the evaluation probe, fluorescence substances that respectively emit fluorescences having different wavelengths are used. Examples of the fluorescence substance include fluorescein, derivatives thereof (for example, fluorescein isothiocyanate (FITC)), phycoerythrin (PE), Texas red (registered trademark) (TR), Cy Dye, rhodamine, and Alexa Fluor (registered trademark).

"Antibody" includes Fab, Fv, scFv, and Fd fragments, chimeric antibodies, humanized antibodies, single-chain antibodies, and fusion proteins including antigen-binding portions of antibodies and non-antibody proteins, but not limited thereto, and includes any isotypic antibodies or immunoglobulins, and antibody fragments that retain specific binding ability to antigens. "Antibody" may further bind to another portion such as a member of a specific binding pair of biotin or the like (member of biotin-avidin specific binding pair). Further, "antibody" also include Fab', Fv, F(ab')2, and other antibody fragments that retain specific binding ability to antigens.

"Polynucleotide" and "nucleic acid" are interchangeably used in the entire description herein, and include DNA molecules (for example, cDNA or genome DNA), RNA molecules, (for example, mRNA), DNA or RNA analogs generated using nucleotide analogs (for example, peptide nucleic acid and non-natural nucleotide analog), and hybrids thereof. "Nucleic acid molecule" may be single-stranded or double-stranded.

"Hybridization" or "hybridize" means to form a hydrogen bond (this can be Watson-Crick hydrogen bond, Hoogsteen hydrogen bond, or reverse Hoogsteen hydrogen bond) between complementary nucleoside bases or complementary nucleotide bases. For example, adenine and thymine are complementary nucleic acid bases that are paired through formation of a hydrogen bond. Herein, "complementary" means ability to form correct pairing between two nucleotides. For example, when a nucleotide at a specific position of a polynucleotide can form a hydrogen bond with a nucleotide at the same position in a DNA molecule, this polynucleotide and this DNA are considered to be complementary to each other at that position. This polynucleotide and this DNA are complementary to each other, when a sufficient number of corresponding positions in the respective molecules are occupied by nucleotides that can form hydrogen bonds with each other. Therefore, the terms "specifically hybridize" and "complementary" are used to indicate a sufficient degree of complementarity or correct pairing that allows stable and specific binding to occur between this polynucleotide and this DNA target.

If a polynucleotide can be hybridized to a base sequence of a detection target region or an evaluation target region under a stringent condition, they are "complementary".

"Stringent condition" means a condition that a polynucleotide is selectively hybridized to a specific nucleic acid sequence and is hardly or not at all hybridized to another sequence. A person skilled in the art could select such a "stringent condition" as appropriate. A "stringent condition" can be set with reference to conditions and the like regarding short chain nucleotide hybridization described in Molecular Cloning, A Laboratory Manual, second edition [J. Sambrook et al., Cold Spring Harbor Laboratory Press, issued in 1989], for example. Examples of such a "stringent condition" include, but not limited thereto, a condition that in an environment of 44° C., hybridization is performed in a pH7.4 solution containing 30 to 70 mass % formamide; and then, washing is performed under a condition of 60° C. or higher by use of 2×SSC (composition of 1×SSC: 0.15 M sodium chloride, 0.015 M sodium citrate, pH7.0).

"Detection target region" is, among DNA sequence regions present in the nucleus of a cell, a DNA sequence region which serves as the target for detection of the presence or absence of any of the abnormalities of gene amplification, deletion, translocation, and inversion.

"Evaluation target region" is, among DNA sequence regions present in the nucleus of a cell, a DNA sequence region that increases in association with DNA replication in S phase of the cell cycle, and in which neither amplification nor sequence change due to genomic abnormality occurs. When detecting an abnormal cell in which gene amplification has occurred, it is sufficient that the evaluation target region is, among DNA sequence regions present in the nucleus of a cell, a part of a DNA sequence region excluding any DNA sequence region where amplification occurs. For example, when detecting an abnormal cell in which Her2 gene amplification has occurred, it is sufficient that a part of a DNA sequence region excluding Her2 gene is set as the evaluation target region, and for example, the centromere region of chromosome 17 may be set as the evaluation target region. When detecting an abnormal cell in which deletion has occurred, it is sufficient that the evaluation target region is, among DNA sequence regions present in the nucleus of a cell, a part of a DNA sequence region excluding any DNA sequence region where deletion occurs. When detecting an abnormal cell in which translocation has occurred, the evaluation target region may be any region on the genome. A DNA sequence region that is moved to another chromosome due to translocation may be set as the evaluation target region, or a DNA sequence region that includes the cut point caused by translocation may be set as the evaluation target region. For example, when detecting an abnormal cell in which BCR-ABL fusion gene is formed as a result of ABL gene at chromosome 9 having been moved to chromosome 22 due to translocation and fused with BCR gene at chromosome 22, BCR gene or ABL gene may be set as the evaluation target region. When detecting an abnormal cell in which inversion has occurred, the evaluation target region may be any region on the genome. A DNA sequence region that is moved due to inversion may be set as the evaluation target region, or a DNA sequence region that includes the cut point caused by inversion may be set as the evaluation target region.

"Nucleic acid staining dye" is a substance that stains the entirety of the nucleic acid in a cell. The nucleic acid staining dye emits fluorescence having a wavelength that is different from the wavelengths of the respective fluorescence substances of the detection probe and the evaluation probe which are hybridized to specific regions of DNA to label the specific regions with the fluorescences, respectively. The nucleic acid staining dye includes intercalaters for specifically staining the nucleic acid and fluorescent dyes that bind to the minor groove. Examples of the intercalater include known cyanin-based, acridine-based, and phenanthridium-based dyes. Examples of the cyanin-based intercalater include SYBR (registered trademark) Green I, and Thiazole orange. Examples of the acridine-based intercalater include Acridin orange. Examples of the phenanthridium-based intercalater include propidium Iodide and Ethidium bromide. Examples of the dye that binds to the minor groove include known dyes such as DAPI, HOECHST, and the like. Examples of HOECHST include HOECHST 33342, HOECHST 33258, and the like.

"Cell" may be a natural cell or an artificially modified cell (for example, fused cell, iPS cell). The cell may be a somatic cell or a germ cell. Examples of such a cell include, but not limited thereto, embryonic stem cell, somatic stem cell, differentiated cell (for example, epidermal cell, pancreatic parenchymal cell, pancreatic duct cell, hepatocyte, blood cell, cardiomyocyte, skeletal muscle cell, osteoblast, skeletal myoblast, neuron, vascular endothelial cell, pigment cell, smooth muscle cell, adipocyte, osteocyte, chondrocyte, etc.). As the cell of animal species, preferably, vertebrate derived cells are used, and more preferably, mammal derived cells are used. Still more preferably, primate (for example, chimpanzee, Japanese macaque, human) derived cells are used. Most preferably, human derived cells are used. When performing detection on cells in a flow cytometer, the detection is preferably performed in a state where cell clusters are disaggregated into individual cells. Preferably, before the detection probe and the evaluation probe are hybridized to specific regions of DNA, the cells are fixed by a polar organic solvent such as methanol or ethanol.

"Sample" means a specimen that includes cells, and in which the detection probe and the evaluation probe having been hybridized to DNA in the cells and the entirety of the nucleic acid in each cell has been stained.

In a sample preparation step, the nucleic acid is stained by the nucleic acid staining dye, and the evaluation probe is caused to be hybridized to the genome, whereby a sample is prepared.

Preferably, before the nucleic acid staining and the hybridization of the evaluation probe, the cells are fixed in order to suppress nucleic acid degradation and the like. For cell fixation, a known fixative such as ethanol, methanol, or formaldehyde can be used.

Before causing the evaluation probe to be hybridized to genome DNA, it is preferable to denature the genome DNA by a known technique such as heating or chemical treatment using a surfactant, to make the genome DNA single stranded. This also applies to the case where both of the evaluation probe and the detection probe (hereinafter, these may be simply collectively referred to as "probe") are used.

After hybridization of the probe has been performed, the detection probe and the evaluation probe that have been nonspecifically hybridized to DNA may be removed by washing. The probe can be washed by use of a solution having a low salt concentration.

In a case of the probe that includes the labeled antibody, a blocking process may be performed to reduce the background before the antibody is caused to react. As a blocking agent, BSA, skim milk, or the like can be used. After the labeled antibody has been caused to react, a B/F separation process may be performed in which the labeled antibody bound to the target substance is separated from the labeled antibody that is not bound to the target substance and thus free, whereby the free labeled antibody may be removed. The B/F separation process can be performed through centrifuging, for example.

In a case of the probe that includes the primary antibody and the labeled secondary antibody, the blocking process and/or the B/F separation process described above can be performed for the reaction between the primary antibody and the polynucleotide of the probe. Further, also when the labeled secondary antibody is caused to react, the blocking process and/or the B/F separation process described above can be performed.

The nucleic acid staining and the hybridization of the evaluation probe may be performed at the same time or may be performed separately. The staining and the hybridization can be performed at the same time by mixing together the cells and a staining reagent that includes the nucleic acid staining dye and the evaluation probe. In a case of the evaluation probe that includes the polynucleotide and the antibody, the nucleic acid staining may be performed at the same time as the hybridization between the polynucleotide and the genome DNA, or may be performed at the same time as the antibody reaction. When the nucleic acid staining and the hybridization of the evaluation probe are performed separately, the order of performing these is not limited in particular.

In a light receiving step, excitation light is applied to the prepared sample, and information of generated fluorescence is obtained. Information of fluorescence generated by applying the excitation light to the nucleic acid staining dye which stains the nucleic acid in each cell, and information of fluorescence generated by applying the excitation light to the fluorescent dye of the evaluation probe are obtained.

In a selection step, on the basis of the fluorescence information from the nucleic acid staining dye and the fluorescent dye of the evaluation probe, an analysis target cell is selected.

As the analysis target cells for the purpose of detecting cells having genomic abnormality, cells can be selected in each of which the proportion between the fluorescence intensity from the nucleic acid staining dye and the fluorescence intensity from the fluorescent dye of the evaluation probe is in a certain range. For example, cells in each of which the proportion between the fluorescence intensity from the nucleic acid staining dye and the fluorescence intensity from the fluorescent dye of the evaluation probe is in a predetermined numerical value range can be selected as the analysis target cells. Other than this, the analysis target cells can be selected in the following manner: in a histogram data having an axis that represents the above-described proportion obtained from each cell in the sample, the proportion of the median thereof is identified; and then, cells in a range having a predetermined width relative to the identified median proportion are selected as the analysis target cells.

When the analysis target cells are to be selected, for example, only measurement data of the analysis target cells may be extracted from measurement data obtained by measuring the respective cells in the sample, or alternatively, only the analysis target cells may be separated from other cells by physical means and collected, from among all the cells in the sample. As the physical means, for example, a configuration may be employed in which bubbles are generated by heat and are caused to collide with cells flowing in a flow path, thereby separating the cells from other cells. Alternatively, a configuration may be employed in which one of bifurcated flow paths is opened/closed to change the direction of the liquid flowing in the flow path, whereby only the desired cells are caused to flow in one flow path to be collected.

Genomic abnormality can be detected on the basis of the fluorescence intensity obtained from the fluorescence substance of the detection probe which has been bound to DNA of each selected cell. For example, genomic abnormality may be detected by calculating the rate between the fluorescence intensity from the fluorescence substance of the detection probe and the fluorescence intensity from the fluorescence substance of the evaluation probe. For example, a cell in which the value obtained by dividing the fluorescence intensity from the fluorescence substance of the detection probe by the fluorescence intensity from the fluorescence substance of the evaluation probe exceeds a threshold may be detected as a cell in which genomic abnormality has occurred. Alternatively, the difference between the fluorescence intensity from the fluorescence substance of the detection probe and the fluorescence intensity from the fluorescence substance of the evaluation probe is calculated, and then, a cell in which the difference exceeds a threshold may be detected as a cell in which genomic abnormality has occurred.

Embodiment 1

Embodiment 1 is obtained by applying the present disclosure to a FISH-based method for detecting, as an abnormal cell, a cell in which only a specific DNA sequence region has been amplified. In Embodiment 1, cells that have become cancerous due to amplification of Her2 gene are detected abnormal cells.

As shown in FIG. 1, a cell detection method for detecting an abnormal cell includes a sample preparation step, a light receiving step, a selection step, and a detection step. Hereinafter, a case will be described in which an operator performs the cell detection method shown in FIG. 1, by using a flow cytometer and a processing apparatus capable of analyzing the intensity of fluorescence obtained by the flow cytometer.

In the sample preparation step in step S11, the operator performs hybridization of the detection probe to the detection target region of DNA in the nucleus, hybridization of the evaluation probe to the evaluation target region of DNA in the nucleus, and staining of the nucleic acid in the cell, thereby preparing a sample. The sample includes cells collected from a subject.

In Embodiment 1, the detection target region is Her2 gene, and the evaluation target region is the sequence of a part of a DNA sequence region excluding Her2 gene in chromosome 17. Hereinafter, the sequence of a part of a DNA sequence region excluding Her2 gene in chromosome 17 will be referred to as "Ch17". It is sufficient that the evaluation target region is, among DNA sequence regions present in the nucleus of a cell, a DNA sequence region that increases in association with replication of DNA in S phase of the cell cycle and in which neither amplification nor sequence change due to genomic abnormality occurs. For example, the evaluation target region may be any region, among DNA sequence regions in the nucleus, excluding any DNA sequence region where amplification occurs. From this viewpoint, an example of the evaluation target region is the centromere region of chromosome 17, for example.

Figure 2A:
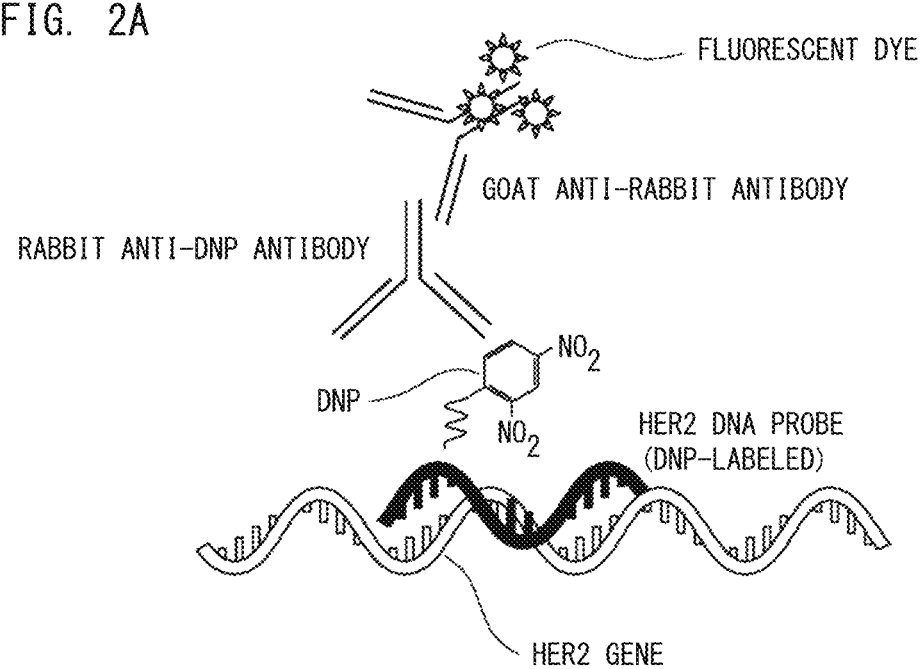
FIG. 2A shows a state in which a detection probe is bound to a detection target region according to Embodiment 1.
Figure 2B:
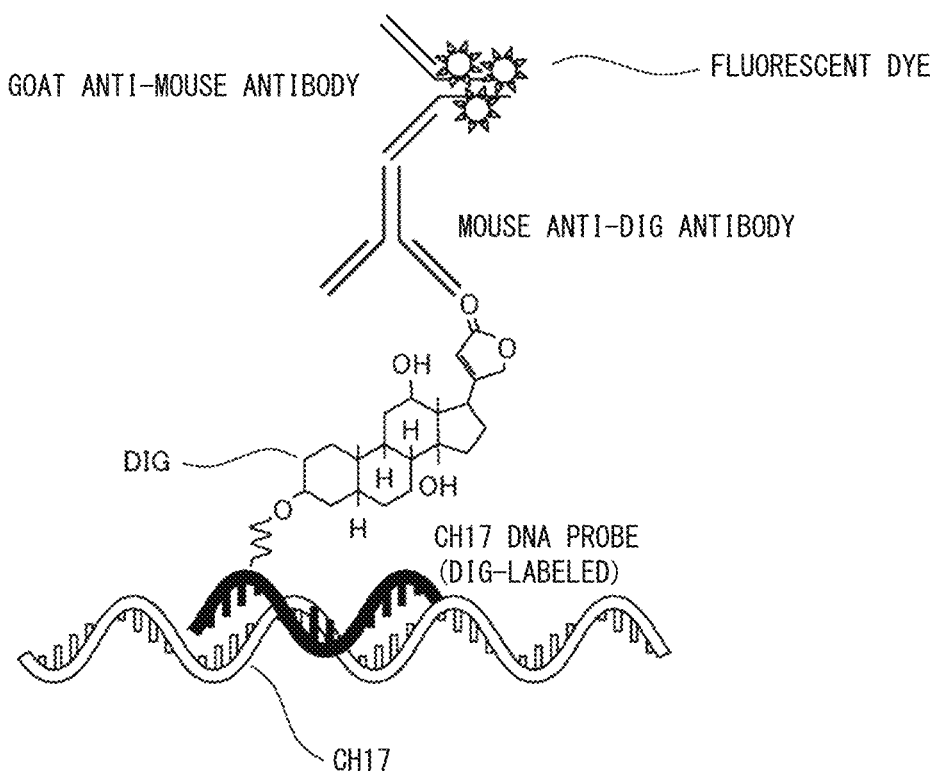
FIG. 2B shows a state in which an evaluation probe is bound to an evaluation target region according to Embodiment 1.

As shown in FIG. 2A, the detection probe includes a polynucleotide (Her2 DNA probe) which specifically binds to Her2 gene being the detection target region; a primary antibody (Rabbit anti-DNP Antibody); a secondary antibody (Goat anti-Rabbit Antibody); and a fluorescent dye (Alexa Fluor (registered trademark) 647). The polynucleotide is labeled with dinitrophenol (DNP). Through the sample preparation step of step S11, the polynucleotide is bound to the detection target region, and the fluorescent dye is bound to the polynucleotide via the primary antibody and the secondary antibody. As shown in FIG. 2B, the evaluation probe includes a polynucleotide (Ch17 DNA Probe) which specifically binds to Ch17 being the evaluation target region; a primary antibody (Mouse anti-DIG Antibody); a secondary antibody (Goat anti-Mouse Antibody); and a fluorescent dye (Alexa Fluor (registered trademark) 488). The polynucleotide is labeled with digoxigenin (DIG). Through the sample preparation step of step S11, the polynucleotide is bound to the evaluation target region, and the fluorescent dye is bound to the polynucleotide via the primary antibody and the secondary antibody. In addition, through the sample preparation step of step S11, the nucleus is stained by a nucleic acid staining dye for specifically staining the nucleic acid, specifically, a fluorescent dye (HOECHST 33342) which binds to the minor groove of AT sequence of DNA. By this dye, the entirety of the nucleic acid in the nucleus is stained.

As the fluorescent dye included in the detection probe, the fluorescent dye included in the evaluation probe, and the fluorescent dye for staining the entirety of the nucleic acid in the nucleus, different kinds of fluorescent dyes are used that respectively generate fluorescences having different wavelengths when lights having predetermined wavelengths are respectively applied thereto.

With reference back to FIG. 1, in the light receiving step of step S12, the operator uses a flow cytometer to cause the sample prepared in step S11 to flow in the flow cell, to cause light to be applied to the sample flowing in the flow cell, and to cause a light receiving unit to receive the fluorescence from the fluorescent dye included in the detection probe, the fluorescence from the fluorescent dye included in the evaluation probe, and the fluorescence from the nucleic acid staining dye. In step S12, instead of the flow cytometer, a fluorescence microscope may be used. As the fluorescence microscope, Axio Imager manufactured by Zeiss can be used, for example. In this case, the operator disposes the sample on a base (for example, slide glass), and operates the microscope to apply light to the sample on the base. As the base, not limited to a slide glass, any support body made of metal or of any other appropriate solid may be used. For example, a base plate made of a silicon wafer may be used.

In step S12, as a result of the light receiving unit receiving fluorescences, with respect to each cell, the intensity of the fluorescence from the fluorescent dye included in the detection probe, the intensity of the fluorescence from the fluorescent dye included in the evaluation probe, and the intensity of the fluorescence from the nucleic acid staining dye are obtained. "Intensity of fluorescence" here means the peak value in the fluorescence signal waveform (the horizontal axis represents time, and the vertical axis represents intensity) outputted from the light receiving unit. As the intensity of fluorescence, not limited to the peak value of the fluorescence signal waveform, the area of the fluorescence signal waveform may be used. As described above, the fluorescent dye included in the detection probe bound to the detection target region, the fluorescent dye included in the evaluation probe bound to the evaluation target region, and the fluorescent dye staining the nucleic acid in the nucleus generate fluorescences respectively having different wavelengths as a result of application of light. Thus, for example, if three kinds of fluorescences having different wavelengths are received by different light receiving units, respectively, it is possible to distinguish the detection target region, the evaluation target region, and the entirety of the nucleus from one another.

Instead of the light receiving step of step S12, an image capturing step and a brightness obtaining step may be performed. In the image capturing step, the operator uses a flow cytometer that can capture particle images, to cause the sample prepared in step S11 to flow in the flow cell, to cause light to be applied to the sample flowing in the flow cell, and to cause an image capturing unit to capture images of the fluorescence from the fluorescent dye included in the detection probe, the fluorescence from the fluorescent dye included in the evaluation probe, and the fluorescence from the nucleic acid staining dye. Accordingly, with respect to each cell, an image of the fluorescence from the fluorescent dye included in the detection probe, an image of the fluorescence from the fluorescent dye included in the evaluation probe, and an image of the fluorescence from the nucleic acid staining dye are obtained. Then, in the brightness obtaining step, the operator uses a processing apparatus to calculate the brightness in each image.

Figure 3A:
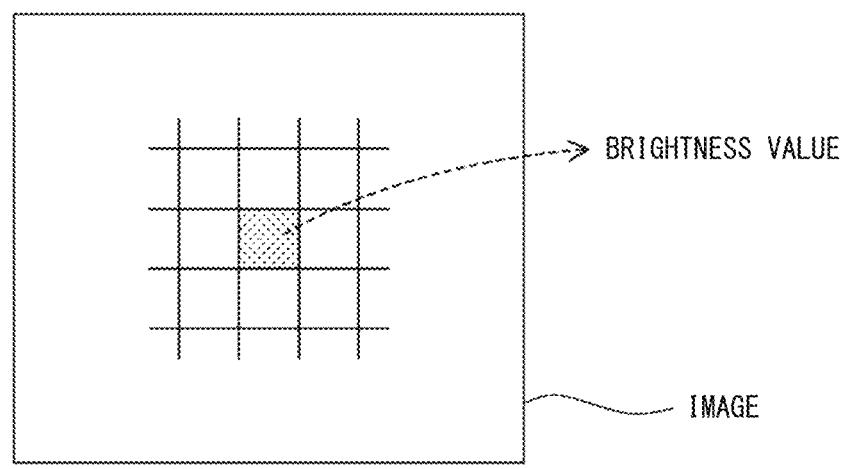
FIG. 3A is a diagram explaining that a brightness value is obtained from each pixel of an image according to a modification of Embodiment 1.

With reference to FIGS. 3A and B, the calculation of the brightness in each image will be described. As shown in FIG. 3A, in the image of fluorescence, a brightness value indicating the brightness/darkness is obtained for each pixel. In a case where the captured image is a monochrome image, a value based on gradation is used as the brightness value, for example. In a case where the captured image is a color image, the captured image is converted into a monochrome image and then a brightness value is obtained, for example. The brightness value is obtained for each of all the pixels on the image.

Figure 3B:
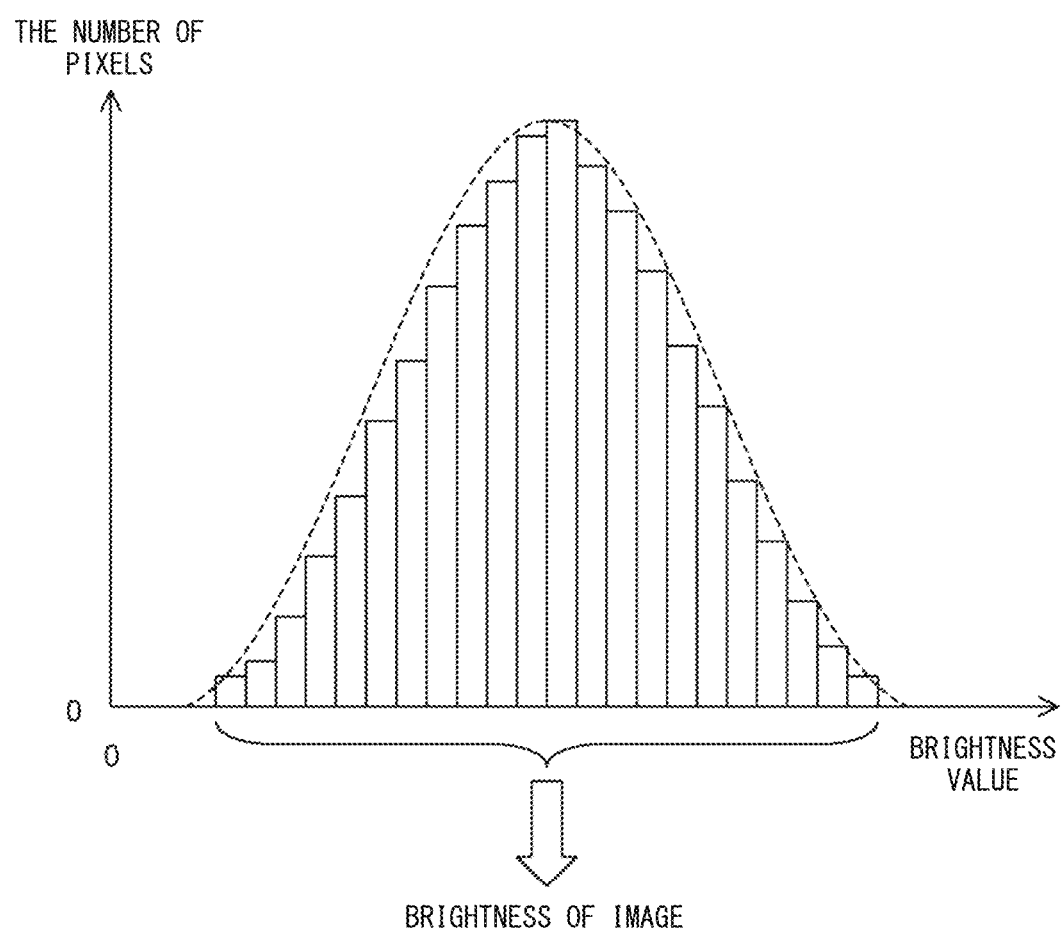
FIG. 3B is a diagram explaining that the brightness of an image is obtained from brightness values according to a modification of Embodiment 1.

Subsequently, for example, as shown in FIG. 3B, on the basis of the brightness values of all the pixels on the image, a histogram is created in which the horizontal axis represents brightness value and the vertical axis represents the number of pixels. In this histogram, a curve represented by a broken line is generated in accordance with the number of pixels, and the area of the range surrounded by this curve is calculated as the brightness of the image. The brightness of the image may be the total of the brightness values of all the pixels. The operator performs calculation as described above by using a processing apparatus, and calculates the brightness in each image. The brightness of the image thus calculated corresponds to the intensity of fluorescence generated by the light receiving unit receiving fluorescences. Therefore, the intensity of fluorescence to be used in the following process may be replaced with the brightness in the image of fluorescence.

Next, in the selection step of step S13, on the basis of the intensity of the fluorescence from the fluorescent dye included in the evaluation probe and the intensity of the fluorescence from the nucleic acid staining dye, the processing apparatus selects analysis target cells. More specifically, in step S13, the processing apparatus determines, as an analysis target cell, a cell in which the intensity of the fluorescence from the fluorescent dye included in the evaluation probe and the intensity of the fluorescence from the nucleic acid staining dye are in a relationship in which the hybridization state of the evaluation probe to the evaluation target region is evaluated as being appropriate. Then, from measurement data obtained by measuring each cell in the sample, the processing apparatus extracts data of intensity of the fluorescence from the fluorescent dye included in the evaluation probe and data of intensity of the fluorescence from the fluorescent dye included in the detection probe, which have been obtained from the analysis target cell.

Figure 4A:
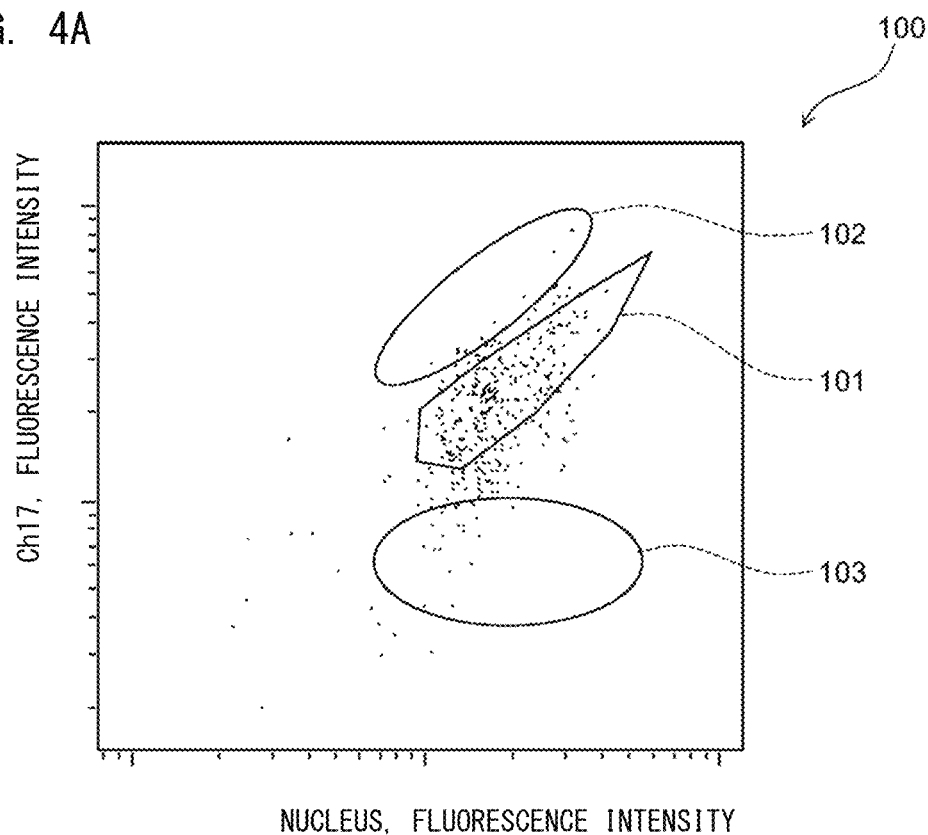
FIG. 4A shows a scattergram and a region for selecting analysis target cells according to Embodiment 1.

As shown in FIG. 4A, in step S13, a scattergram 100 is created in which the vertical axis represents the intensity of the fluorescence from the fluorescent dye included in the evaluation probe, and the horizontal axis represents the intensity of the fluorescence from the nucleic acid staining dye. In the scattergram 100, a dot is plotted so as to correspond to each cell included in the sample. In the scattergram 100, a region 101 is set in which the proportion between the intensity of the fluorescence from the fluorescent dye included in the evaluation probe and the intensity of the fluorescence from the nucleic acid staining dye is evaluated as being in a predetermined range.

Figure 4B:
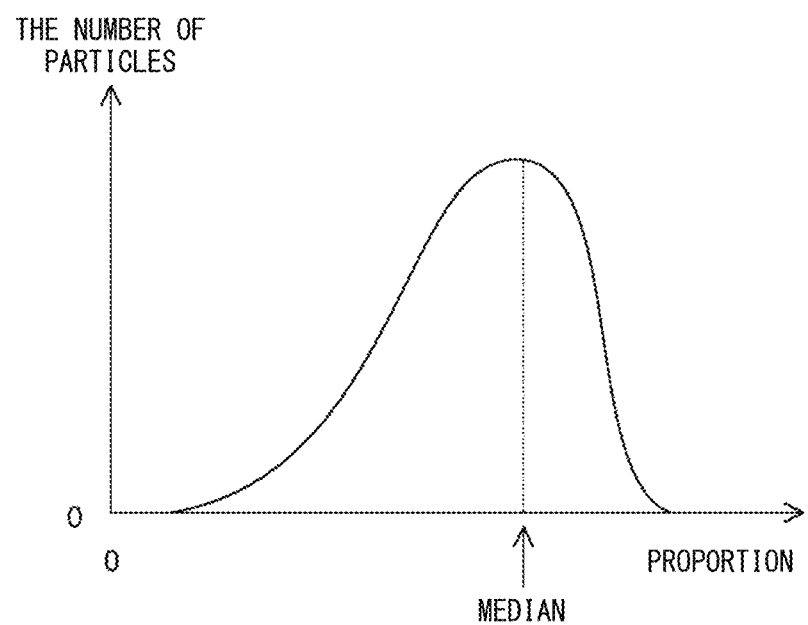
FIG. 4B is a histogram to be used for calculating the median according to Embodiment 1.

The region 101 is set as follows, for example. For each cell, calculated is the proportion between the intensity of the fluorescence from the fluorescent dye included in the evaluation probe and the intensity of the fluorescence from the nucleic acid staining dye. As shown in FIG. 4B, on the basis of the proportion calculated for each of all the cells, a histogram is created in which the horizontal axis represents the proportion and the vertical axis represents the number of particles. In the created histogram, the median proportion is identified. Then, the region that surrounds the particles in the range having a predetermined width relative to the identified median proportion is set as the region 101.

Figure 5A:
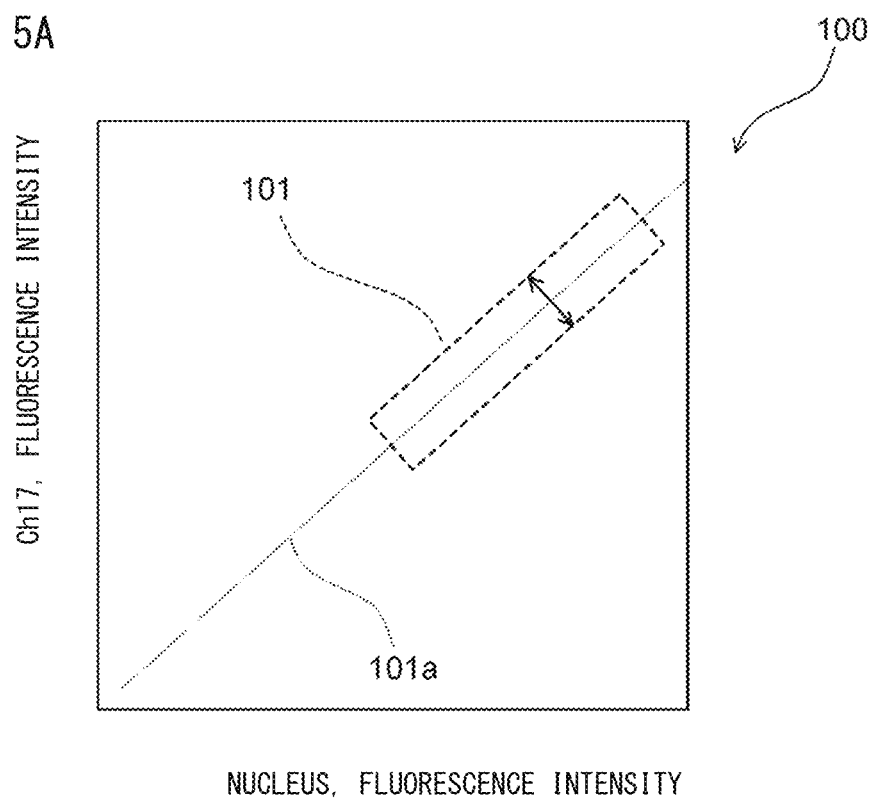
FIG. 5A is a modification of the region for selecting analysis target cells according to Embodiment 1.
Figure 5B:
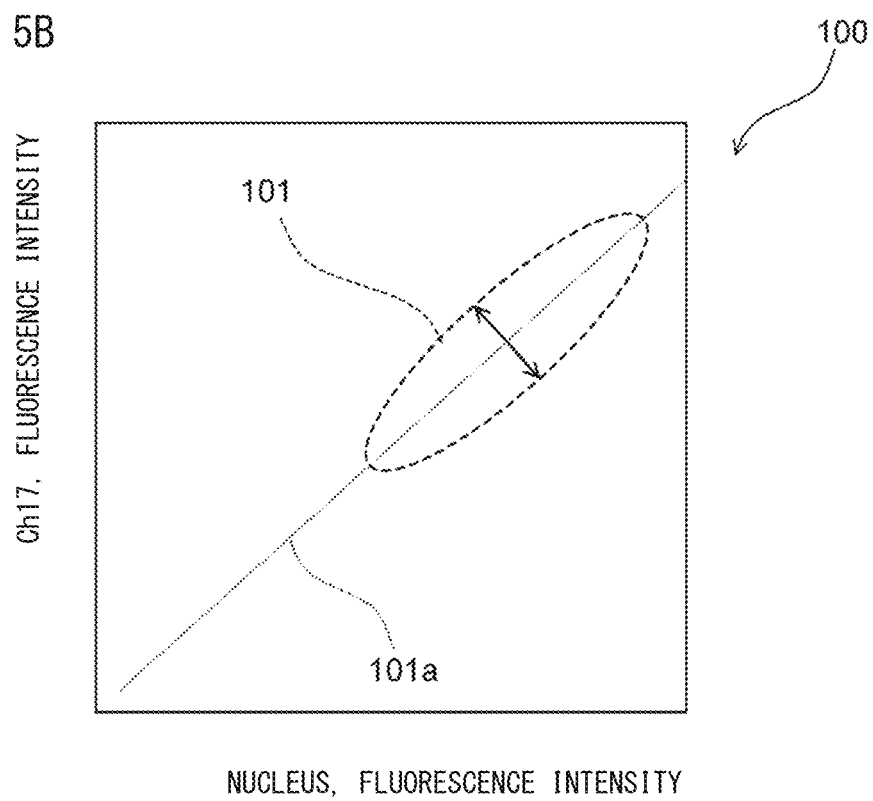
FIG. 5B is a modification of the region for selecting analysis target cells according to Embodiment 1.

The shape of the region 101 set in the scattergram 100 is not limited to the shape shown in FIG. 4A, and may be a shape shown in FIG. 5A or 5B. The region 101 shown in FIG. 5A is a region that has a predetermined width across a straight line 101a assumed as the center line. The slope of the straight line 101a is the median proportion calculated as above, and the straight line 101a passes through the origin. That is, the straight line 101a is a straight line whose vertical axis values and horizontal axis values can be regarded as being proportional to each other. The region 101 shown in FIG. 5B is a region surrounded by a curve and having a predetermined width across the straight line 101a assumed as the center line. It is sufficient that the width of the region 101 across the straight line 101a assumed as the center line in FIG. 5A, 5B is set so as to allow accurate selection of cells in which appropriate hybridization has occurred. For example, the width of the region 101 is set so as to include cells in 3 to 5% range of variation across the straight line 101a assumed as the center line.

Here, unlike the cases of the detection target region and the evaluation target region, the staining of the entirety of the nucleus is not realized by binding of a fluorescence labeled probe through hybridization, but is performed by the nucleic acid staining dye. The staining is performed to the entirety of the nucleic acid in the nucleus by the nucleic acid staining dye, but the amount of a gene, such as Her2 gene, that is locally amplified is small relative to the entirety of the nucleic acid. Therefore, the intensity of fluorescence obtained from the entirety of the nucleic acid staining dye changes, substantially in accordance with increase of the amount of nucleic acid in the nucleus associated with DNA replication in S phase of the cell cycle.

Meanwhile, as described above, the evaluation target region is, among DNA sequence regions present in the nucleus of a cell, a DNA sequence region in which neither amplification nor sequence change due to genomic abnormality occurs. Since the evaluation target region increases in association with DNA replication in S phase of the cell cycle, if appropriate hybridization of the evaluation probe to the evaluation target region has occurred in the sample preparation step of step S11, the intensity of the fluorescence from the fluorescent dye included in the evaluation probe changes, in accordance with the intensity of the fluorescence from the entirety of the nucleic acid staining dye. Therefore, cells in which appropriate hybridization has occurred are included in the region 101 for which it can be considered that the proportion between the intensity of the fluorescence from the fluorescent dye included in the evaluation probe and the intensity of the fluorescence from the nucleic acid staining dye is in a predetermined range.

However, actually, appropriate hybridization not always occurs in all the cells. In a case of a cell in which appropriate hybridization has not occurred, the intensity of the fluorescence from the fluorescent dye included in the evaluation probe changes, not only corresponding to the intensity of the fluorescence from the nucleic acid staining dye alone, but also corresponding to the hybridization state. That is, cells in which appropriate hybridization has not occurred are included in regions 102 and 103 located outside the region 101 in the vertical direction.

The region 102 above the region 101 and the region 103 below the region 101 include cells for which it can be considered that appropriate hybridization of the evaluation probe to the evaluation target region has not occurred therein. The region 102 is a region in which the fluorescence from the fluorescent dye included in the evaluation probe has high intensity, and thus, the region 102 includes cells for which it is considered that nonspecific binding of the evaluation probe has occurred therein. Nonspecific binding of the evaluation probe occurs when the evaluation probe binds to a DNA sequence region other than the evaluation target region, for example. The region 103 is a region in which the fluorescence from the fluorescent dye included in the evaluation probe has low intensity, and thus, the region 103 includes cells for which it is considered that decrease of staining efficiency of the evaluation probe has occurred therein. Decrease of the staining efficiency of the evaluation probe is caused by poor hybridization of the evaluation probe, for example.

In the selection step of step S13, on the basis of all the cells in the sample plotted on the scattergram 100, i.e., on the basis of all the cells included in the current sample, the region 101 is set. Then, the cells in the region 101 are selected as the analysis target cells. Alternatively, the region 101 may be a region that is set in advance on the basis of a previous sample and that is stored in the processing apparatus. In a case where the region 101 is set in advance, a plot is made on the scattergram at the time when the intensity of fluorescence of one cell is obtained, and if this cell is included in the region 101, this cell may be selected as the analysis target cell.

In the selection step of step S13 described above, for convenience of explanation, the scattergram 100 is created in the processing apparatus. However, at the actual selection of cells, the scattergram 100 is not used, and the processing apparatus performs processing, using a virtual coordinate space having an axis of the intensity of the fluorescence from the nucleic acid staining dye and an axis of the intensity of the fluorescence from the fluorescent dye included in the evaluation probe, thereby selecting the analysis target cells. Also in the description below, without using the scattergram, processing is performed in the virtual coordinate space having two axes of fluorescence intensities, whereby cell selection is performed. It should be noted that the processing apparatus may select cells by creating a scattergram as described above.

In the selection step of step S13, only the cells in which appropriate hybridization of the evaluation probe to the evaluation target region has occurred are selected. When appropriate hybridization of the evaluation probe to the evaluation target region has occurred, it is considered that hybridization of the detection probe to the detection target region has also appropriately occurred. Thus, through the selection step of step S13, cells in which appropriate hybridizations of the evaluation probe and the detection probe have occurred are selected.

With reference to the figure showing examples of cells in FIG. 6, description will be given of the intensity of fluorescence from cells in the regions 101 to 103 of the scattergram 100 shown in FIG. 4A.

"Bright field" shows a bright field image of a cell. "Ch17" shows a captured image of the fluorescence from the fluorescent dye included in the evaluation probe, i.e., the fluorescence corresponding to Ch17. "Nucleus" shows a captured image of the fluorescence from the nucleic acid staining dye. "Her2" shows a captured image of the fluorescence from the fluorescent dye included in the detection probe, i.e., the fluorescence corresponding to Her2 gene. Four images arranged in the horizontal direction are images obtained from a single cell. Five cells shown in FIG. 6 are normal cells in which Her2 gene is not amplified and in which double-strand DNA is present. Therefore, it can be assumed that in any of these cells, if appropriate hybridization has occurred, two bright points corresponding to Ch17 and two bright points corresponding to Her2 gene can be identified.

With reference to the images of each cell in the region 101, the presence of two Ch17 bright points and two Her2 gene bright points is clearly observed. With reference to the images of the cell in the region 102, the Ch17 bright point and the Her2 gene bright point are difficult to be identified because fluorescence is generated from the entirety of the cell. With reference to the images of each cell in the region 103, the Ch17 bright point and the Her2 gene bright point are difficult to be identified because the intensity of fluorescence is not sufficient.

Therefore, in the case of the cells in the regions 102 and 103, bright points cannot be appropriately evaluated. Thus, in the detection step described later, abnormal cells cannot be accurately detected. That is, in the case of the cells in the regions 102 and 103, there is a risk that false-positive and/or false-negative are determined. However, according to Embodiment 1, in the selection step of step S13, the cells included the region 101 of the scattergram 100, i.e., only the cells for which it is considered that appropriate hybridization has occurred therein, can be selected as the analysis target cells. Therefore, poorly stained cells are less likely to be mixed in the selected analysis target cells, and thus, abnormal cells can be accurately detected in the detection step.

With reference back to FIG. 1, in the detection step of step S14, the operator uses the processing apparatus to detect abnormal cells from the analysis target cells, on the basis of the fluorescence from the fluorescent dye included in the detection probe. More specifically, in step S14, on the basis of the ratio between the intensity of the fluorescence from the fluorescent dye included in the detection probe, and the intensity of the fluorescence from the fluorescent dye included in the evaluation probe, the processing apparatus detects abnormal cells from the analysis target cells. Specifically, for each cell, the intensity of the fluorescence from the fluorescent dye included in the detection probe is divided by the intensity of the fluorescence from the fluorescent dye included in the evaluation probe. Then, if the result of the division exceeds a predetermined threshold, it is determined that the detection target region has been amplified in the cell. Then, the cell in which the detection target region has been amplified is detected as an abnormal cell. The amplification of the detection target region may be determined only on the basis of the intensity of the fluorescence from the fluorescent dye included in the detection probe exceeding a predetermined threshold.

In a case where images of the fluorescence from the fluorescent dye included in the detection probe and the fluorescence from the fluorescent dye included in the evaluation probe are captured and obtained by the image capturing unit, abnormal cells may be detected on the basis of the distribution of the fluorescence from the fluorescent dye included in the detection probe and the distribution of the fluorescence from the fluorescent dye included in the evaluation probe in the image. For example, the number of bright points corresponding to the detection probe is divided by the number of bright points corresponding to the evaluation probe. Then, if the result of the division exceeds a predetermined threshold, the cell may be detected as an abnormal cell. Alternatively, if the difference between the number of bright points corresponding to the detection probe and the number of bright points corresponding to the evaluation probe exceeds a predetermined threshold, the cell may be detected as an abnormal cell. Still alternatively, the total area, in the image, of the fluorescence from the fluorescent dye included in the detection probe is divided by the total area, in the image, of the fluorescence from the fluorescent dye included in the evaluation probe. Then, if the result of the division exceeds a predetermined threshold, the cell may be detected as an abnormal cell.

In the selection step of step S13, the cells for which it is considered that appropriate hybridization has occurred are selected as the analysis target cells. In the detection step of step S14, with respect to each selected cell, whether or not the cell is an abnormal cell is determined. Thus, if the detection step is performed after the selection step, only with respect to each of the cells in which appropriate hybridization has occurred, whether or not the cell is an abnormal cell is determined. Thus, the accuracy of detecting abnormal cells in the detection step can be enhanced.

As described above, in Embodiment 1, cells that have become cancerous due to amplification of Her2 gene can be accurately detected as abnormal cells. Therefore, in a case of breast cancer in which Her2 gene is amplified in accordance with progress of disease condition or the like, a medical doctor or the like can accurately determine the disease condition on the basis of the detected abnormal cells. Since Her2 gene is one of the prognostic factors of breast cancer, a medical doctor or the like can appropriately determine a therapeutic strategy for the patient on the basis of the detected abnormal cells. In Embodiment 1, Her2 gene is set as the detection target region serving as an index for therapeutic strategy determination. However, not limited thereto, another disease may be set as the treatment target, and in accordance with the target disease, another gene may be set as the detection target region serving as an index for determining a therapeutic strategy.

Verification of Embodiment 1

Next, verification of Embodiment 1 performed by the present inventors will be described.

1. Preparation of Sample

As control cells, MCF7 which is Her2 gene amplification negative was used. As abnormal cells, SK-BR-3 which is Her2 gene amplification positive was used.

(1) Fixation $2 \times 10^6$ of MCF7 cells were put in a 1.5 mL tube, and $2 \times 10^6$ SK-BR-3 cells were put in a 1.5 mL tube. In a 24° C. room temperature environment, each tube was centrifuged at 1500 rpm for 1 minute, and the supernatant was removed. 700 μL of PBS was put in each tube, to resuspend the content. While lightly agitating, 300 μL of Carnoy's solution was added to each tube, to obtain Carnoy's solution having a final concentration of 30%. Carnoy's solution is a solution in which the ratio between methanol and acetic acid is 3:1. In a 4° C. environment, sedimentation of the content was prevented with each tube being agitated, until 20 minutes elapsed.

In a 24° C. room temperature environment, each tube was centrifuged at 1500 rpm for 1 minute, and the supernatant was removed. 300 μL of PBS was put in each tube, to resuspend the content. While lightly agitating, 700 μL of Carnoy's solution was added to each tube, to obtain Carnoy's solution having a final concentration of 70%. In a 4° C. environment, sedimentation of the content was prevented with each tube being agitated, until 20 minutes elapsed.

(2) Hybridization

288 μL of HybReady (manufactured by Ventana, #780-4409) and 12 μL of Her2 DNA cocktail probe (manufactured by Ventana, #109509) were mixed together, to prepare a reagent for hybridization. Her2 DNA cocktail probe includes Her2 DNA probe labeled with dinitrophenol (DNP); and Ch17 DNA probe labeled with digoxigenin (DIG). The Ch17 DNA probe labeled with DIG manufactured by Ventana is configured to be hybridized to the sequence of a part of a DNA sequence region excluding Her2 gene in chromosome 17.

In a 24° C. room temperature environment, each tube of (1) was centrifuged at 1500 rpm for 1 minute, and the supernatant was removed. 1 mL of Reaction Buffer (manufactured by Ventana, #950-300) was put in each tube, and washing was performed. This washing was performed twice. 120 μL of the reagent for hybridization was added to each tube, to suspend the content well. The content of each tube was dispensed into two 0.2 mL tubes. That is, two tubes each containing MCF7 cells were prepared, and two tubes each containing SK-BR-3 cells were prepared. In a 95° C. environment, each tube was heated for 5 minutes by a thermal cycler, to dissociate DNA into single strands. In a 44° C. environment, hybridization was conducted overnight (about 16 hours).

(3) Probe Washing

2×SSC (manufactured by Ventana, #650-012) was heated to 65° C. by a heat block in advance. 100 μL of 2×SSC was added to each tube of (2). In a 24° C. room temperature environment, each tube was centrifuged at 1500 rpm for 1 minute. After the centrifugation, the supernatant in each tube was removed. The procedure of adding 100 μL of 2×SSC to each tube; heating each tube by a thermal cycler for 3 minutes in a 65° C. environment; centrifuging each tube at 1500 rpm for 1 minute in a 24° C. room temperature environment; and removing the supernatant, was performed three times in total. 100 μL of Reaction Buffer was put in each tube, to resuspend the content.

(4) Blocking

As a blocking reagent, 3 mL of a 1% BSA/Reaction buffer was prepared. In a 24° C. room temperature environment, each tube of (3) was centrifuged at 1500 rpm for 1 minute, and the supernatant was removed. 100 µL of the blocking reagent was added to each tube, to suspend the content. Blocking was performed for 20 minutes in a 37° C. environment.

(5) Primary Antibody Reaction

24 µL of Rabbit Anti DNP Ab and 216 µL of Mouse Anti DIG Ab were mixed together, to prepare a primary antibody reaction reagent. In a 24° C. room temperature environment, each tube of (4) was centrifuged at 1500 rpm for 1 minute, and the supernatant was removed. In order to prepare samples for detection, 80 µL of the primary antibody reaction reagent was added to two tubes of all the tubes, and the content was caused to be suspended. In order to prepare samples for setting regions described later, not the primary antibody reaction reagent but Reaction buffer was added to the remaining two tubes, and the content was caused to be suspended. In a 37° C. environment, primary antibody reaction was performed for 20 minutes.

(6) Secondary Antibody/Nucleus Staining Reaction

1 µL of Anti-Mouse IgG-Alexa 488 (manufactured by Cell Signaling Technology, #4408S) being a fluorescence labeled antibody, 1 µL of Anti-Rabbit IgG-Alexa 647 (manufactured by Cell Signaling Technology, #4414S) being a fluorescence labeled antibody, 1 µL of HOECHST 33342 (manufactured by Dojindo, #346-07951), and 1000 µL of the blocking reagent were mixed together, to prepare a secondary antibody/nucleus staining reaction reagent. In a 24° C. room temperature environment, each tube of (5) was centrifuged at 1500 rpm for 1 minute, and the supernatant was removed. 100 µL of the secondary antibody/nucleus staining reaction reagent was added to each tube, to suspend the content. In a 37° C. environment, secondary antibody/nucleus staining reaction was performed for 20 minutes in a light-blocked state.

(7) Measurement Sample Preparation

In a 24° C. room temperature environment, each tube of (6) was centrifuged at 1500 rpm for 1 minute, and the supernatant was removed. The procedure of adding 100 µL of TBST to each tube; centrifuging each tube at 1500 rpm for 1 minute in a 24° C. room temperature environment; and removing the supernatant, was performed three times in total. 100 µL of the blocking reagent was added to each tube, to resuspend the content.

2. Measurement by Flow Cytometer

The sample in each of the four tubes having been subjected to the procedure of (1) to (7) was measured by an imaging flow cytometer (ImageStream$^X$ Mark II Imaging Flow Cytometer) manufactured by Amnis. Laser lights respectively having wavelengths of 405 nm, 488 nm, 642 nm, and 785 nm were applied to the sample flowing in the flow cell of the flow cytometer. Then, light corresponding to the fluorescence from the fluorescent dye included in the detection probe, light corresponding to the fluorescence from the fluorescent dye included in the evaluation probe, light corresponding to the fluorescence from the nucleic acid staining dye, and light corresponding to the bright field were received, and the intensity and the image of each fluorescence were obtained.

3. Setting Regions for Removing Unnecessary Particles

Using the two tubes in which Reaction buffer had been added instead of the primary antibody reaction reagent in the procedure (5) above, regions for removing unnecessary particles were set. These two tubes were caused to respectively hold a sample that contained control cells not having been subjected to the primary antibody reaction, and a sample that contained abnormal cells not having been subjected to the primary antibody reaction.

The sample not having been subjected to the primary antibody reaction was caused to flow in the flow cell. Then, for each particle contained in the sample, obtained were a bright field image; the intensity of the light corresponding to the fluorescence from the fluorescent dye included in the evaluation probe; the intensity of the light corresponding to the fluorescence from the fluorescent dye included in the detection probe; and the intensity of the light corresponding to the fluorescence from the nucleic acid staining dye. On the basis of the sample containing the control cells, and the sample containing the abnormal cells, as shown in FIGS. 7A, 7B, a scattergram 110 whose vertical axis represented the sphericity of the particle in the bright field image, and whose horizontal axis represented the area of the particle in the bright field image. When the sphericity is closer to 1, the shape of the particle is closer to a sphere. Each cell that can be the analysis target has a sphericity close to 1 and has a predetermined area. Thus, a region 111 of the scattergram 110 was set as the region where cells that could be the analysis target were distributed.

Subsequently, on the basis of the particles included in the region 111 of the scattergram 110, as shown in FIG. 7C, 7D, a scattergram 120 was created whose vertical axis represented the intensity of the light corresponding to the fluorescence from the fluorescent dye included in the evaluation probe, and whose horizontal axis represented the intensity of the light corresponding to the fluorescence from the nucleic acid staining dye. Only very weak fluorescence is generated from most of minute particles. Thus, the group of cells having fluorescence of a predetermined intensity or higher was set as the analysis target. Therefore, a region 121 of the scattergram 120 was set as the region where cells that could be the analysis target were distributed, and a region 122 of the scattergram 120 was set as the region where minute particles that could not be the analysis target were distributed.

Subsequently, on the basis of the particles included in the region 121 of the scattergram 120, as shown in FIG. 7E, 7F, a scattergram 130 was created whose vertical axis represented the intensity of the light corresponding to the fluorescence from the fluorescent dye included in the detection probe, and whose horizontal axis represented the intensity of the j light corresponding to the fluorescence from the fluorescent dye included in the evaluation probe. From the cells in the sample not having been subjected to the primary antibody reaction, although intrinsic fluorescence is slightly generated, fluorescence having an intensity higher than the predetermined intensity is not generated. Thus, in the scattergram 130, a region 132 which included substantially all the cells in this sample was set as the region where the cells not having been subjected to the primary antibody reaction were distributed. Then, in the scattergram 130, a region 131 in which the values in the vertical axis and in the horizontal axis are both greater than those in the region 132 was set as the region where the cells that could be the analysis target were distributed.

4. Selection of Cells to be Used as the Analysis Target

Using the two tubes in which the primary antibody reaction reagent had been added in the procedure (5) above, cells to be used as the analysis target were selected. These two tubes were caused to respectively hold a sample that contained control cells, and a sample that contained abnormal cells. Each sample was caused to flow in the flow cell. Then, for each particle contained in the sample, obtained were a bright field image; the intensity of the light corresponding to the fluorescence from the fluorescent dye included in the evaluation probe; the intensity of the light corresponding to the fluorescence from the fluorescent dye included in the detection probe; and the intensity of the light corresponding to the fluorescence from the nucleic acid staining dye.

Subsequently, on the basis of the sample containing the control cells and the sample containing the abnormal cells, as shown in FIG. 8A, 8B, the scattergram 110 similar to that in FIG. 7A, 7B was created. In the scattergram 110 of this case, the region 111 similar to that in FIG. 7A, 7B was set. Subsequently, on the basis of the particles included in the region 111 in FIG. 8A, 8B, the scattergram 120 similar to that in FIG. 7C, 7D was created as shown in FIG. 8C, 8D. In the scattergram 120 of this case, the region 121 similar to that in FIG. 7C, 7D was set. Subsequently, on the basis of the particles included in the region 121 in FIG. 8C, 8D, the scattergram 130 similar to that in FIG. 7E, 7F was created as shown in FIG. 8E, 8F. In the scattergram 130 of this case, the region 131 similar to that in FIG. 7E, 7F was set.

Subsequently, on the basis of the particles included in the region 131 in FIG. 8E, 8F, the scattergram 100 similar to that in FIG. 4A was created as shown in FIG. 9A, 9B. As described with reference to FIG. 4A, in the scattergram 100 of this case, the region 101 was set for which it could be considered that the proportion between the intensity of the fluorescence from the fluorescent dye included in the evaluation probe and the intensity of the fluorescence from the nucleic acid staining dye was in a predetermined range. Then, the particles included in the region 101 in FIG. 9A, 9B were selected as the analysis target cells.

Thus, as a result of the narrowing-down of the cells to be the analysis target as shown in FIGS. 8A to 8F, unnecessary particles were removed. As a result, by using the region 101 in FIG. 9A, 9B, it was possible to accurately select the cells for which it was considered that appropriate hybridization had occurred therein.

5. Sensitivity and Specificity Based on Analysis Target Cells

Figure 10:
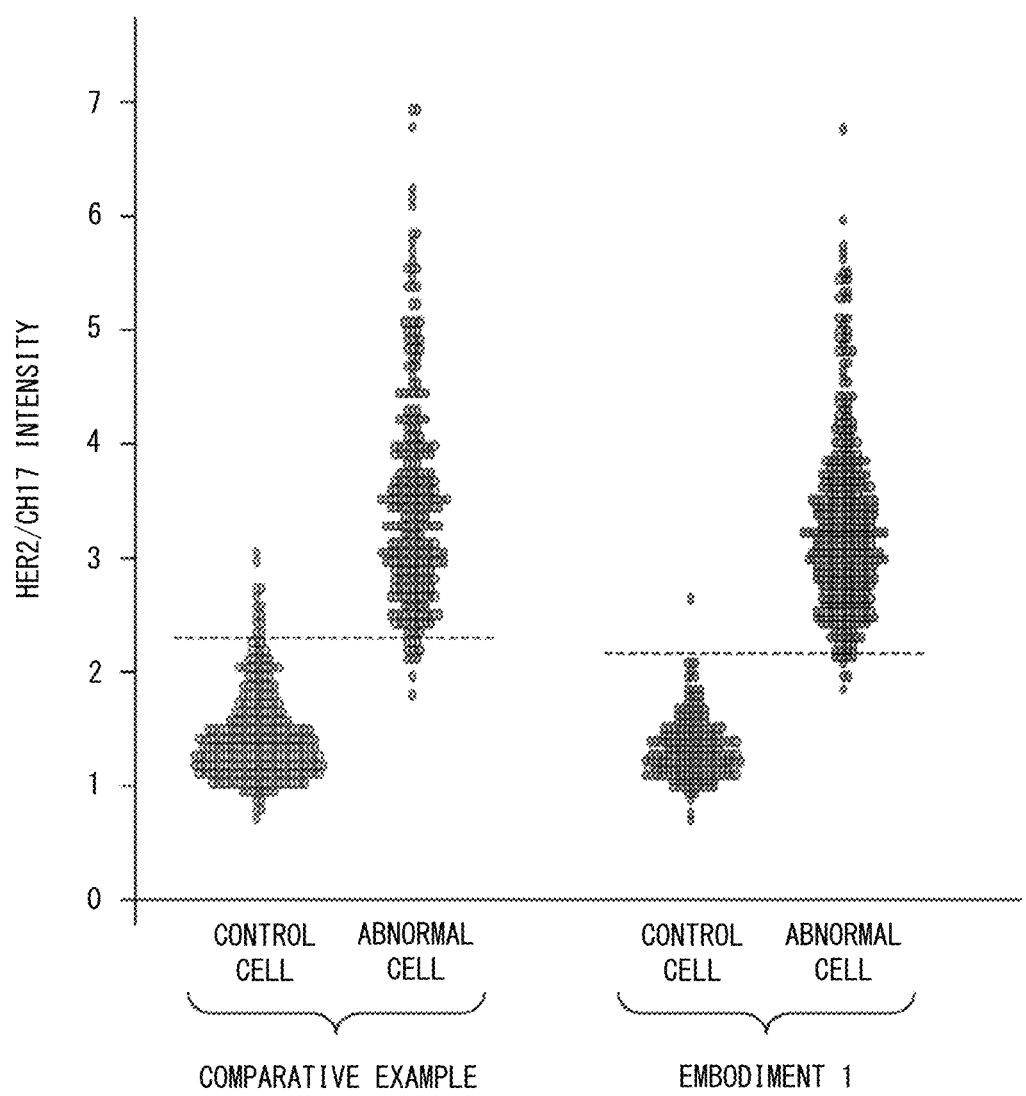
FIG. 10 shows verification results according to Embodiment 1 and Comparative example.

With respect to each of the analysis target cells finally selected in 4 described above, a value was obtained by dividing the intensity of the fluorescence from the fluorescent dye included in the detection probe by the intensity of the fluorescence from the fluorescent dye included in the evaluation probe. As shown in FIG. 10, the values obtained by the above division according to Embodiment 1 were plotted, classified as control cell or abnormal cell.

In addition, in FIG. 10, values obtained by the above-described division for the respective analysis target cells selected in Comparative example were plotted, classified as control cell or abnormal cell. In Comparative example, without using the scattergram 100 shown in FIG. 9A, 9B, the particles included in the region 131 in FIG. 8E, 8F were set as the analysis target. That is, compared with Embodiment 1, Comparative example omitted the step of selecting the cells in which appropriate hybridization had occurred.

In each of Embodiment 1 and Comparative example, as indicated by the broken line in FIG. 10, a threshold for the value obtained by the division was set so as to realize the maximum sensitivity and the maximum specificity. Sensitivity is the value obtained by dividing the number of cells determined as abnormal because the cells are above the threshold, by the actual number of abnormal cells contained in the sample. Specificity is the value obtained by dividing the number of cells determined as normal because the cells are below the threshold, by the number of control cells contained in the sample. In the case of Comparative example, sensitivity and specificity were both 94.5%. In the case of Embodiment 1, sensitivity and specificity were both 99.1%, and were better than those of Comparative example.

It should be noted that another value may be used as the threshold. For example, the maximum value of the values obtained by the division of the respective control cells in Embodiment 1 may be used as the threshold. Alternatively, the minimum value of the values obtained by the division of the respective abnormal cells in Embodiment 1 may be used as the threshold.

As described above, according to the present verification, if the cells in which appropriate hybridization has occurred are selected by using the region 101 of the scattergram 100 as in Embodiment 1, sensitivity and specificity can be improved. Thus, according to Embodiment 1, abnormal cells and normal cells can be accurately detected, and thus, drug therapy effect can be accurately monitored.

Embodiment 2

Embodiment 2 is obtained by applying the present disclosure to a FISH-based method for detecting, as an abnormal cell, a cell in which translocation has occurred. The method for detecting an abnormal cell in which translocation has occurred will be described using an example of translocation that occurs between chromosome 9 and chromosome 22, the translocation observed in chronic myeloid leukemia.

Figure 11A:
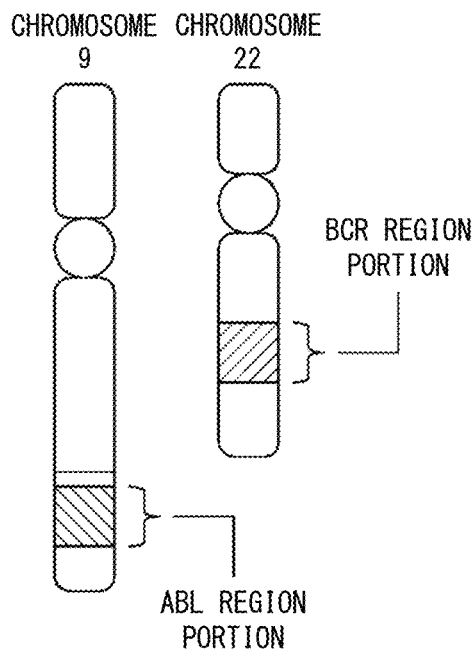
FIG. 11A is a schematic diagram showing one example of fluorescence labeling when performing determination of translocation on the basis of dual fusion according to Embodiment 2.

As shown in FIG. 11A, in a case of a normal cell, i.e., a translocation negative cell, the sequence of ABL gene is in chromosome 9, and the sequence of BCR gene is in chromosome 22. Hereinafter, the sequence of BCR gene will be referred to as "BCR region portion" and the sequence of ABL gene will be referred to as "ABL region portion". When translocation has occurred, the ABL region portion is moved to chromosome 22. As a result, in a case of an abnormal cell, i.e., a translocation positive cell, a BCR-ABL fusion gene is formed as shown in FIG. 11B.

Figure 11B:
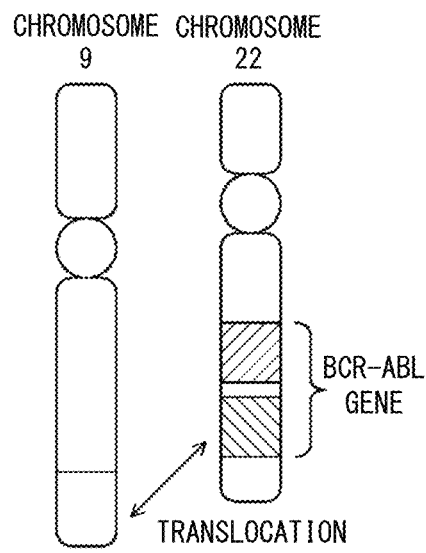
FIG. 11B is a schematic diagram showing one example of fluorescence labeling when performing determination of translocation on the basis of dual fusion according to Embodiment 2.
Figure 11C:
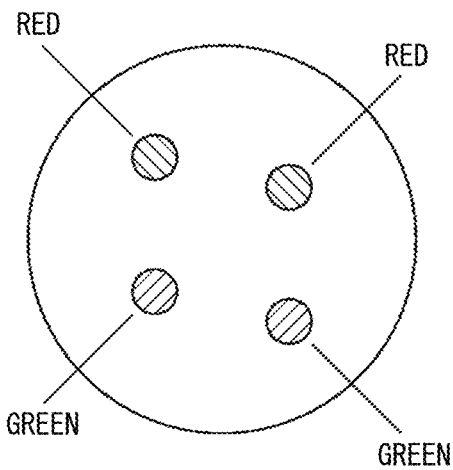
FIG. 11C is a schematic diagram showing one example of a merged fluorescence image when performing determination of translocation on the basis of dual fusion according to Embodiment 2.
Figure 11D:
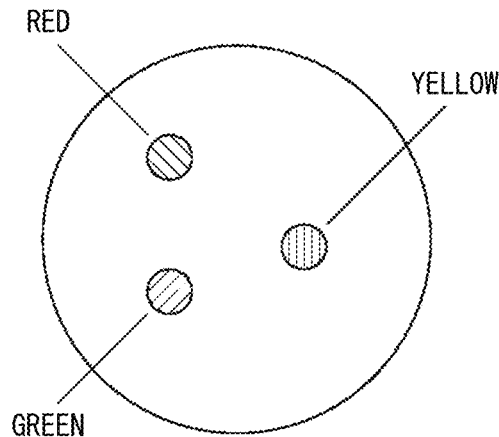
FIG. 11D is a schematic diagram showing one example of a merged fluorescence image when performing determination of translocation on the basis of dual fusion according to Embodiment 2.

Since the translocation occurs in this manner, the ABL region portion is labeled with fluorescence so as to generate red fluorescence, and the BCR region portion is labeled with fluorescence so as to generate green fluorescence as shown in FIG. 11A, 11B, for example. Then, the image of a normal cell becomes as shown in FIG. 11C, and the image of an abnormal cell becomes as shown in FIG. 11D. The cell image shown in FIG. 11C, 11D is obtained by combining an image based on the red fluorescence generated from the cell and an image based on the green fluorescence generated from the cell. In the case of FIG. 11C, since the red bright point and the green bright point are separated from each other, it is seen that the cell is a normal cell. On the other hand, in the case of FIG. 11D, due to so-called dual fusion, the red bright point and the green bright point overlap each other, thus causing a yellow bright point. Accordingly, in the case of FIG. 11D, it is seen that the cell is an abnormal cell in which BCR-ABL fusion gene has been formed. Thus, the medical doctor or the like can diagnose the possibility of chronic myeloid leukemia.

Figure 12A:
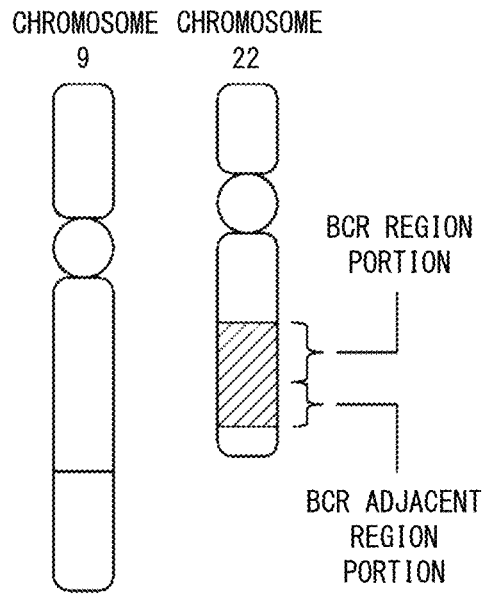
FIG. 12A is a schematic diagram showing one example of fluorescence labeling when performing determination of translocation on the basis of break-apart according to Embodiment 2.
Figure 12B:
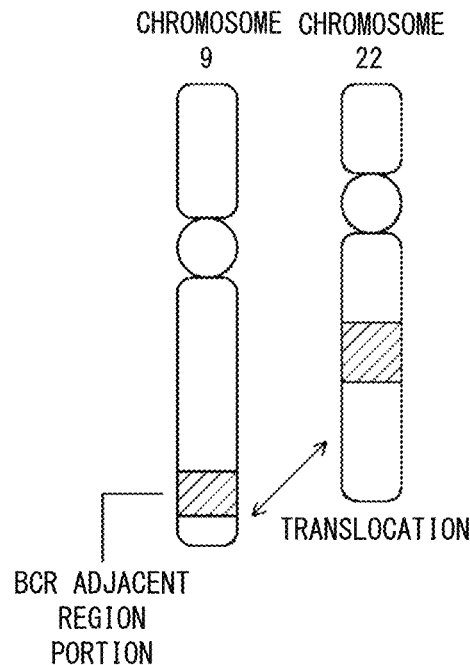
FIG. 12B is a schematic diagram showing one example of fluorescence labeling when performing determination of translocation on the basis of break-apart according to Embodiment 2.

As shown in FIG. 12A, 12B, in order to detect translocation of the ABL region portion to chromosome 22, the BCR region portion and a nucleic acid sequence adjacent to the BCR region portion may be each labeled with fluorescence so as to generate green fluorescence, for example. Hereinafter, the nucleic acid sequence adjacent to the BCR region portion will be referred to as "BCR adjacent region portion". Then, the image of a normal cell becomes as shown in FIG. 12C, and the image of an abnormal cell becomes as shown in FIG. 12D.

Figure 12C:
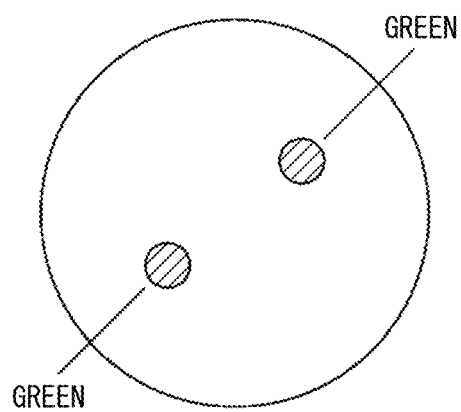
FIG. 12C is a schematic diagram showing one example of merged fluorescence image when performing determination of translocation on the basis of break-apart according to Embodiment 2.
Figure 12D:
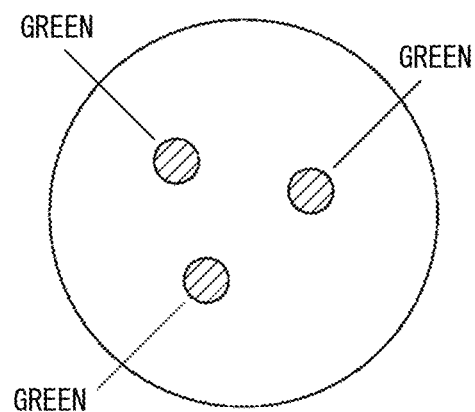
FIG. 12D is a schematic diagram showing one example of merged fluorescence image when performing determination of translocation on the basis of break-apart according to Embodiment 2.

As shown in FIG. 12C, in a case of a normal cell, DNA in the nucleus is double-stranded, and thus, two green bright points appear, according to the state shown in FIG. 12A. On the other hand, as shown in FIG. 12D, in a case of an abnormal cell, due to separation of chromosome, so-called break-apart, the BCR adjacent region portion has been cut from chromosome 22 and moved to chromosome 9, whereby the number of the green bright points has increased. In this case, the ABL region portion in chromosome 9 is moved to the place in chromosome 22 where the BCR adjacent region portion has been. Accordingly, in the case of FIG. 12D, it is seen that the cell is an abnormal cell. It should be noted that the ABL region portion and a nucleic acid sequence adjacent to the ABL region portion may be labeled with fluorescence so as to generate green fluorescence. Also in this case, as in FIG. 12C, 12D, an abnormal cell caused by break-apart can be detected.

Also in a case of determining the dual fusion and the break-apart as described above, the process steps of step S11 to S14 shown in FIG. 1 are performed, whereby abnormal cells are detected.

In a case of determination based on dual fusion, gene sequences are labeled with fluorescence as shown in FIG. 11A. In this case, the evaluation target region is the BCR region portion or the ABL region portion. If the evaluation target region is the BCR region portion, the detection target region is set to the ABL region portion. If the evaluation target region is the ABL region portion, the detection target region is set to the BCR region portion. That is, it is sufficient that the combination of the detection target region and the evaluation target region is the BCR region portion and the ABL region portion.

Also in this case, as in Embodiment 1, in the sample preparation step of step S11, the evaluation probe is bound to the evaluation target region and the detection probe is bound the detection target region through hybridization. Therefore, as in Embodiment 1, through steps S11 to S13, cells in which appropriate hybridization has occurred can be selected on the basis of the intensity of the fluorescence from the fluorescent dye included in the evaluation probe and the intensity of the fluorescence from the nucleic acid staining dye.

In the detection step of step S14, in order to determine the distributions of the ABL region portion and the BCR region portion, an image of the fluorescence from the fluorescent dye included in the detection probe and an image of the fluorescence from the fluorescent dye included in the evaluation probe are used. Therefore, in Embodiment 2, these images are obtained in the light receiving step of step S12.

In step S14, on the basis of the distribution of the fluorescence from the fluorescent dye included in the detection probe and the distribution of the fluorescence from the fluorescent dye included in the evaluation probe in the images obtained in step S12, the processing apparatus detects abnormal cells from the analysis target cells. Specifically, if the position of a bright point based on the detection probe and the position of a bright point based on the evaluation probe overlap each other, thus causing a bright point of a predetermined color in the combined image as shown in FIG. 11D, the processing apparatus determines that translocation has occurred. Then, the processing apparatus detects, as an abnormal cell, the cell in which translocation has occurred. Alternatively, with the cell images displayed on a display unit, the operator may determine, through visual observation, a cell in which the position of a bright point based on the detection probe and the position of a bright point based on the evaluation probe are close to each other or overlapped each other, as an abnormal cell in which translocation has occurred.

In a case of determination based on break-apart, the BCR region portion and a nucleic acid sequence adjacent to the BCR region portion are each labeled with fluorescence as shown in FIG. 12A. In this case, the evaluation target region is the BCR region portion or the BCR adjacent region portion. If the evaluation target region is the BCR region portion, the detection target region is set to the BCR adjacent region portion. If the evaluation target region is the BCR adjacent region portion, the detection target region is set to the BCR region portion. That is, it is sufficient that the combination of the detection target region and the evaluation target region is the BCR region portion and the BCR adjacent region portion. It should be noted that the combination of the detection target region and the evaluation target region may be the ABL region portion and a nucleic acid sequence adjacent to the ABL region portion.

Also in this case, in the sample preparation step of step S11, the evaluation probe is bound to the evaluation target region, and the detection probe is bound to the detection target region through hybridization. However, the evaluation probe and the detection probe of this case are configured to be hybridized to the BCR region portion and the BCR adjacent region portion, and thus have substantially the same configuration. Then, as in the case of dual fusion, through steps S11 to S13, cells in which appropriate hybridization has occurred are selected on the basis of the intensity of the fluorescence from the fluorescent dye included in the evaluation probe and the fluorescence from the nucleic acid staining dye.

In step S14, the processing apparatus detects abnormal cells from the analysis target cells on the basis of the distribution of the fluorescence from the fluorescent dye included in the detection probe and the distribution of the fluorescence from the fluorescent dye included in the evaluation probe in the obtained images. As shown in FIG. 12B, in a case where the detection target region or the evaluation target region has been moved to another chromosome, it is considered that translocation has occurred. Thus, as shown in FIG. 12D, if the number of the bright point based on the detection probe and the evaluation probe has increased, it is determined that translocation has occurred. Then, the cell in which translocation has occurred is detected as an abnormal cell. Alternatively, with the cell images displayed on a display unit, the operator may detect, through visual observation, a cell in which translocation has occurred.

Also in Embodiment 2, with respect to each cell for which it is considered that appropriate hybridization has occurred, whether or not the cell is an abnormal cell is determined. Thus, as in Embodiment 1, the accuracy of detecting abnormal cells can be enhanced. In addition, in Embodiment 2, the abnormal cell in which translocation has occurred between chromosome 9 and chromosome 22 is accurately detected, and thus, the medical doctor or the like can accurately determine the disease condition of myeloid leukemia.

Embodiment 3

Embodiment 3 is obtained by applying the present disclosure to a FISH-based method for detecting, as an abnormal cell, a cell in which deletion has occurred.

In a case of a normal cell, i.e., a deletion negative cell, a predetermined DNA sequence region is in a predetermined chromosome. However, in a case of an abnormal cell, i.e., a deletion positive cell, the predetermined DNA sequence region is lost from the chromosome. When detecting deletion, the detection target region is set to be the sequence of at least a part of a DNA sequence region that is deleted, and the evaluation target region is set to be the sequence of a part of a DNA sequence region excluding the DNA sequence region that is deleted. Thus, as in Embodiment 1, cells for which it is considered that appropriate hybridization has occurred can be selected. In addition, when the processing apparatus has determined that the intensity of the fluorescence from the fluorescent dye included in the detection probe is lower than or equal to a predetermined threshold, the processing apparatus can detect the abnormal cell in which deletion has occurred. Alternatively, with the images displayed on a display unit, the operator may detect, through visual observation, the abnormal cell in which deletion has occurred.

Embodiment 4

Embodiment 4 is obtained by applying the present disclosure to a FISH-based method for detecting, as an abnormal cell, a cell in which inversion has occurred in a chromosome.

In the case of inversion, the order of the DNA base sequence on a chromosome is partially inversed. Thus, for example, a probe that binds to both of a specific gene and a DNA sequence region adjacent thereto is mixed in the sample. Then, if fluorescence from the fluorescent dye included in the probe is detected, it is possible to determine that the cell is a normal cell in which inversion has not occurred. If the fluorescence from the fluorescent dye included in the probe is not detected, it can be considered that the gene has been cut from the chromosome and inversed and thus binding of the probe has not occurred. Therefore, it is possible to determine that the cell is an abnormal cell in which inversion has occurred. When detecting inversion, the detection target region is set to a region that extends across the specific gene and the DNA sequence region adjacent thereto, and the evaluation target region is set to the specific gene where inversion occurs.

As shown in FIG. 13, the present disclosure can be applied to detections of abnormal cells by determining various genomic abnormalities (gene amplification, translocation, deletion, inversion, and the like).

Embodiment 5

Embodiment 5 is obtained by applying the present disclosure to a cell detection apparatus which detects abnormal cells on the basis of the cell detection method according to Embodiment 1.

Figure 14:
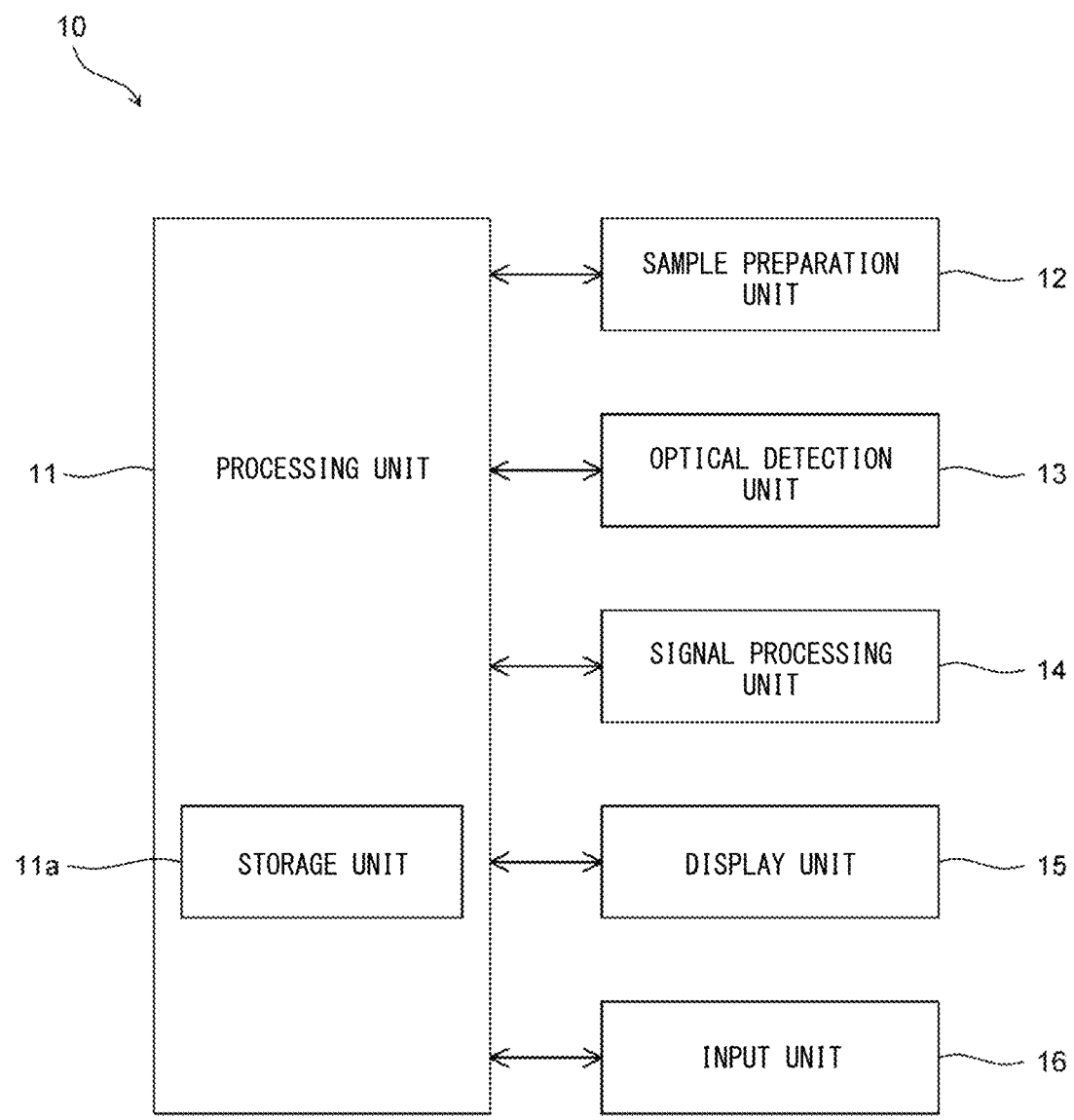
FIG. 14 is a block diagram showing a configuration of a cell detection apparatus according to Embodiment 5.

As shown in FIG. 14, a cell detection apparatus 10 includes a processing unit 11, a sample preparation unit 12, an optical detection unit 13, a signal processing unit 14, a display unit 15, and an input unit 16.

The processing unit 11 is implemented by a microcomputer and a CPU, etc.; and a storage unit 11a. The storage unit 11a is implemented by a RAM, a ROM, a hard disk, and the like. In the storage unit 11a, process programs to be executed by the processing unit 11 are stored. The processing unit 11 transmits/receives signals to/from the components of the cell detection apparatus 10 to control the components. The sample preparation unit 12 prepares a sample by mixing cells and reagents.

Figure 15:
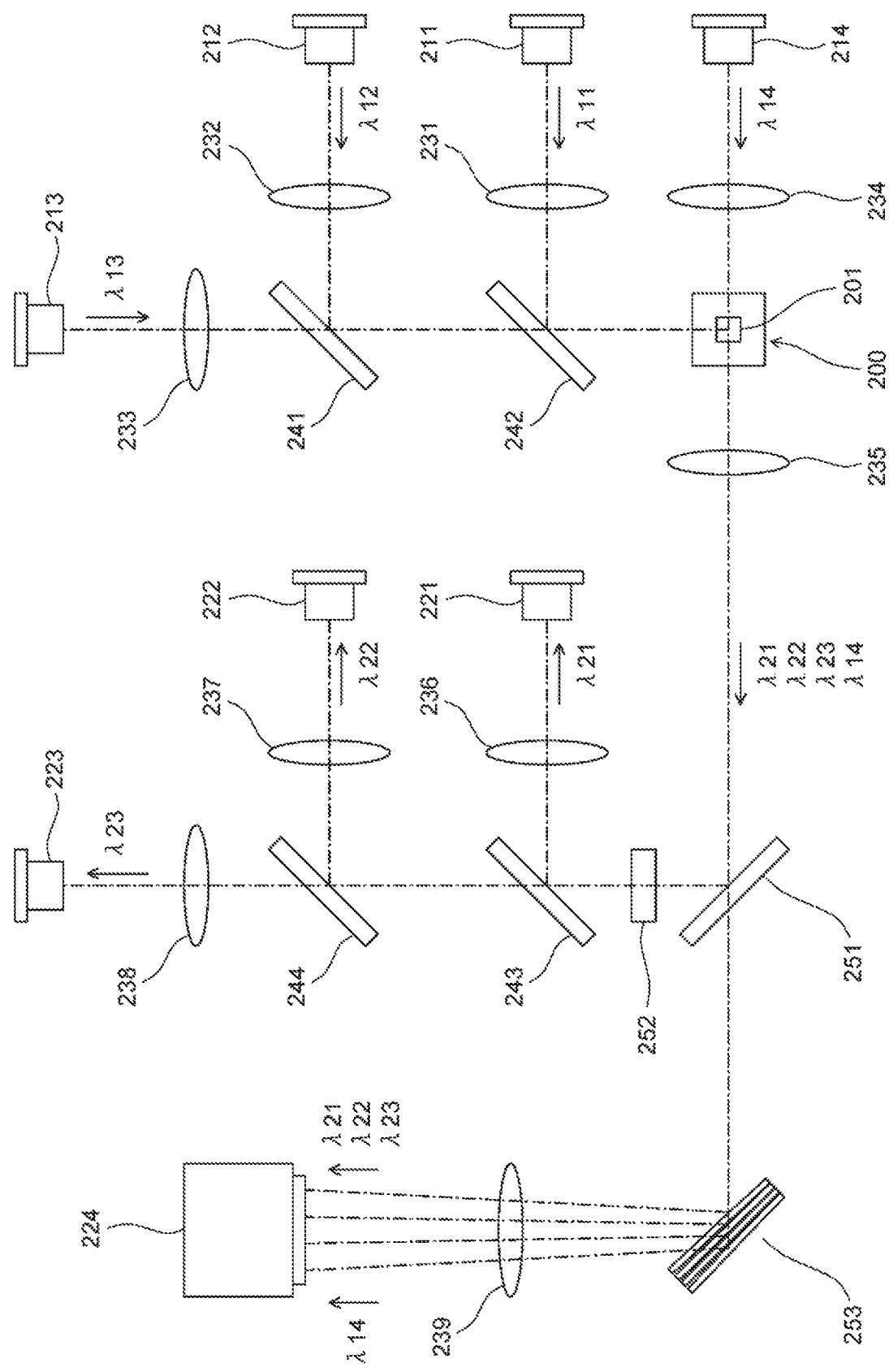
FIG. 15 is a schematic diagram showing a configuration of an optical detection unit according to Embodiment 5.

As shown in FIG. 15, the optical detection unit 13 includes a flow cell 200, light sources 211 to 214, light receiving units 221 to 223, an image capturing unit 224, condenser lenses 231 to 239, dichroic mirrors 241 to 244, a half mirror 251, a filter 252, and an optical unit 253.

The light sources 211 to 214 are each implemented by a semiconductor laser light source. Lights emitted from the light sources 211 to 214 are laser lights having wavelengths $\lambda 11$ to $\lambda 14$, respectively. The wavelengths $\lambda 11$ to $\lambda 14$ are respectively 405 nm, 488 nm, 642 nm, and 785 nm, for example. The condenser lenses 231 to 234 condense lights emitted from the light sources 211 to 214, respectively. The dichroic mirror 241 reflects light having the wavelength $\lambda 12$, and allows light having the wavelength $\lambda 13$ to pass therethrough. The dichroic mirror 242 reflects light having the wavelength $\lambda 11$, and allows lights having the wavelengths $\lambda 12$ and $\lambda 13$ to pass therethrough. Thus, lights having the wavelengths $\lambda 11$ to $\lambda 14$ emitted from the light sources 211 to 214 are applied to the sample flowing in a flow path 201 of the flow cell 200.

When lights having the wavelengths $\lambda 11$ to $\lambda 13$ are applied to the sample flowing in the flow cell 200, fluorescences are generated from the fluorescent dyes staining each cell. When light having the wavelength $\lambda 11$ is applied to the nucleic acid staining dye, fluorescence having a wavelength $\lambda 21$ is generated. When light having the wavelength $\lambda 12$ is applied to the fluorescent dye in the evaluation probe, fluorescence having a wavelength $\lambda 22$ is generated. When light having the wavelength $\lambda 13$ is applied to the fluorescent dye in the detection probe, fluorescence having a wavelength $\lambda 23$ is generated. When light having the wavelength $\lambda 14$ is applied to the sample flowing in the flow cell 200, this light passes through each cell. The light having the wavelength $\lambda 14$ and having passed through the cell is used for generation of a bright field image.

The condenser lens 235 condenses the fluorescences having the wavelengths $\lambda 21$ to $\lambda 23$ generated from the sample flowing in the flow cell 200, and light having the wavelength $\lambda 14$ and having passed through the sample flowing in the flow cell 200. The half mirror 251 allows substantially a half of the lights having passed through the condenser lens 235 to pass through the half mirror 251, and reflects substantially a half thereof to the filter 252.

The filter 252 allows the fluorescences having the wavelengths $\lambda 21$ to $\lambda 23$ to pass therethrough, and blocks unnecessary light. The dichroic mirror 243 reflects the fluorescence having the wavelength $\lambda 21$, and allows the fluorescences having the wavelengths $\lambda 22$ and $\lambda 23$ to pass therethrough. The dichroic mirror 244 reflects the fluorescence having the wavelength $\lambda 22$ and allows the fluorescence having the wavelength $\lambda 23$ to pass therethrough. The condenser lenses 236 to 238 condense fluorescences having wavelengths $\lambda 21$ to $\lambda 23$, respectively. The light receiving units 221 to 223 receive fluorescences having the wavelengths $\lambda 21$ to $\lambda 23$ and output signals corresponding to the intensities of the received fluorescences, respectively. The light receiving units 221 to 223 are each implemented by a photomultiplier. Since the light receiving units 221 to 223 are each implemented by the photomultiplier, the light receiving units 221 to 223 can generate signals corresponding to the intensities of the fluorescences with high sensitivity.

The optical unit 253 is composed of four dichroic mirrors in combination. The four dichroic mirrors of the optical unit 253 reflect the fluorescences having the wavelengths $\lambda 21$ to $\lambda 23$ and the light having the wavelength $\lambda 14$ at angles slightly different from one other, to be separated on the light receiving surface of the image capturing unit 224. The condenser lens 239 condenses the fluorescences having the wavelengths $\lambda 21$ to $\lambda 23$ and the light having the wavelength $\lambda 14$. The image capturing unit 224 is implemented by a TDI (time delay integration) camera. The image capturing unit 224 receives the fluorescences having the wavelengths λ21 to λ23 and the light having the wavelength λ14. Then, the image capturing unit 224 outputs, as image capture signals, pieces of image information of each particle which correspond to the fluorescences having the wavelengths λ21 to λ23 and the light having the wavelength λ14, respectively.

With reference back to FIG. 14, the signal processing unit 14 is implemented by a storage unit and a plurality of circuits for processing signals. On the basis of the signal outputted from each of the light receiving units 221 to 223, the signal processing unit 14 calculates the intensities of the fluorescences for each particle. The processing unit 11 stores the intensities of the fluorescences calculated for each particle, into the storage unit 11a. On the basis of the image capture signals outputted from the image capturing unit 224, the processing unit 11 generates images of each particle, and stores the generated images into the storage unit 11a, for each particle. The display unit 15 is implemented by a display and displays detection results and the like of abnormal cells. The input unit 16 is implemented by a mouse and a keyboard. The operator inputs instructions to the cell detection apparatus 10 via the input unit 16.

Figure 16:
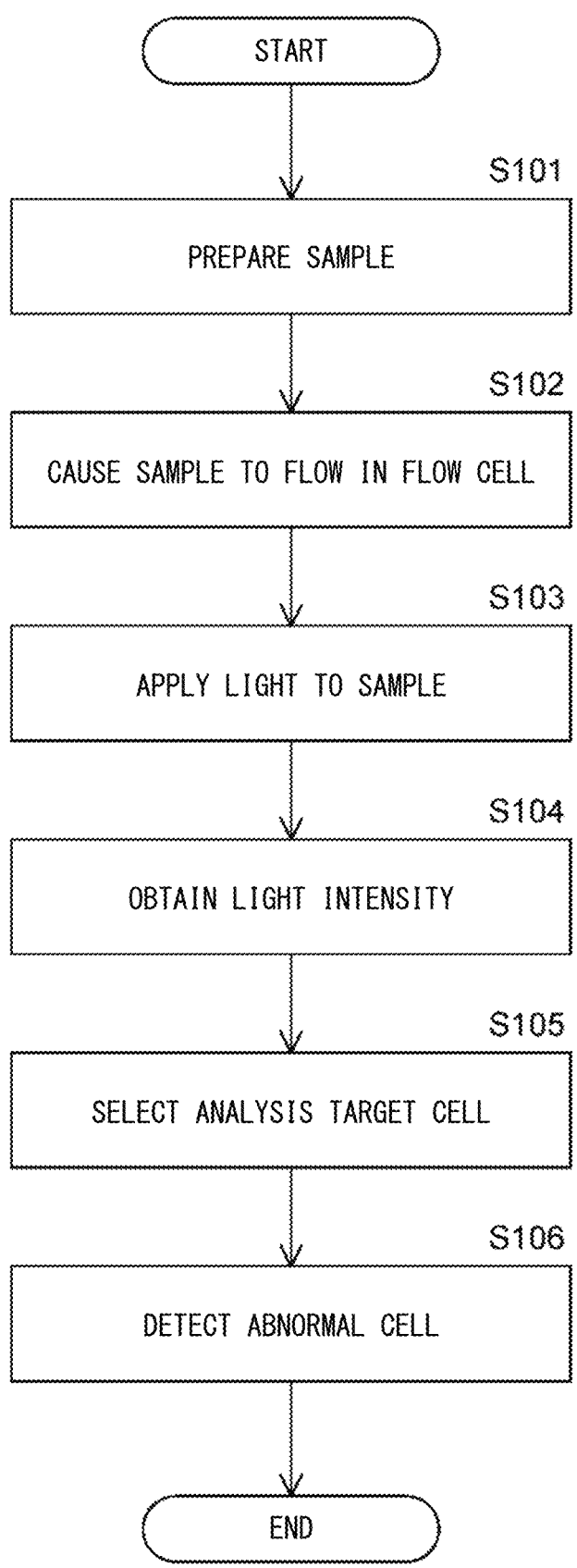
FIG. 16 is a flow chart showing an abnormal cell detection process to be performed by a cell analyzer according to Embodiment 5.

Next, with reference to FIG. 16, an abnormal cell detection process performed by the cell detection apparatus 10 will be described. The abnormal cell detection process is executed by the processing unit 11 controlling the components of the cell detection apparatus 10.

In step S101, the processing unit 11 drives the sample preparation unit 12, and causes the sample preparation unit 12 to prepare a sample by mixing cells; a reagent including the detection probe to be hybridized to the detection target region in each cell; a reagent including the evaluation probe to be hybridized to the evaluation target region in each cell; and a reagent including the nucleic acid staining dye. Accordingly, as shown in FIGS. 2A and 2B, the detection probe including the fluorescent dye binds to the detection target region, and the evaluation probe including the fluorescent dye binds to the evaluation target region. In step S102, the processing unit 11 causes the sample prepared in step S101 to flow in the flow cell 200. In step S103, the processing unit 11 drives the light sources 211 to 214 to apply lights to the sample flowing in the flow cell 200. In step S104, the processing unit 11 causes the light receiving units 221 to 223 to receive fluorescences having the wavelengths λ21 to λ23 generated from each particle in the sample, and obtains intensities of the fluorescences having wavelengths λ21 to λ23.

In step S105, as in step S13 of Embodiment 1, on the basis of the intensity of the fluorescence from the fluorescent dye included in the evaluation probe and the intensity of the fluorescence from the nucleic acid staining dye, the processing unit 11 selects analysis target cells. Specifically, on the basis of the intensities of the fluorescences having the wavelengths λ21 and λ22 calculated by the signal processing unit 14, the processing unit 11 selects the cells in the region 101 of the scattergram 100, as analysis target cells. Also in this case, the processing unit 11 does not actually use the scattergram 100, but performs processing, using a virtual coordinate space having two axes of intensities of fluorescences having wavelengths λ21 and λ22, thereby selecting analysis target cells. Also in this case, as shown in the verification of Embodiment 1, it is preferable to remove unnecessary particles.

In step S106, as in step S14 of Embodiment 1, the processing unit 11 detects abnormal cells from the analysis target cells, on the basis of the fluorescence from the fluorescent dye included in the detection probe. Specifically, the processing unit 11 uses the intensities of the fluorescences having the wavelengths λ22 and λ23 calculated by the signal processing unit 14. For each analysis target cell, the processing unit 11 divides the intensity of the fluorescence having the wavelength λ23 by the intensity of the fluorescence having the wavelength λ22. Then, the processing unit 11 detects cells for each of which the result of the division exceeds a predetermined threshold, as abnormal cells in which the detection target region has been amplified. Alternatively, in step S106, the processing unit 11 may obtain bright points in each image generated from the image capture signal from the image capturing unit 224, and may detect abnormal cells on the basis of the bright points.

Also in Embodiment 5, a cell in which translocation, deletion, or inversion as described in Embodiments 2 to 4 has occurred may be detected as an abnormal cell. In a case of translocation, the processing unit 11 obtains the distribution of the fluorescence on the basis of the images generated from the image capture signals from the image capturing unit 224, and detects an abnormal cell in which translocation has occurred, on the basis of the fluorescence distribution. In a case of deletion or inversion, the processing unit 11 detects a cell in which the intensity of the fluorescence from the fluorescent dye included in the detection probe is lower than or equal to a predetermined threshold, as an abnormal cell in which deletion or inversion has occurred. Alternatively, the processing unit 11 may obtain bright points in the images generated from the image capture signals from the image capturing unit 224, and may detect a cell in which the number of the bright points is smaller than that of a normal cell, as an abnormal cell in which deletion or inversion has occurred.

The processing unit 11 may cause the display unit 15 to display a visual observation result input screen 300 for receiving a result of images classified on the basis of visual observation.

Figure 17:
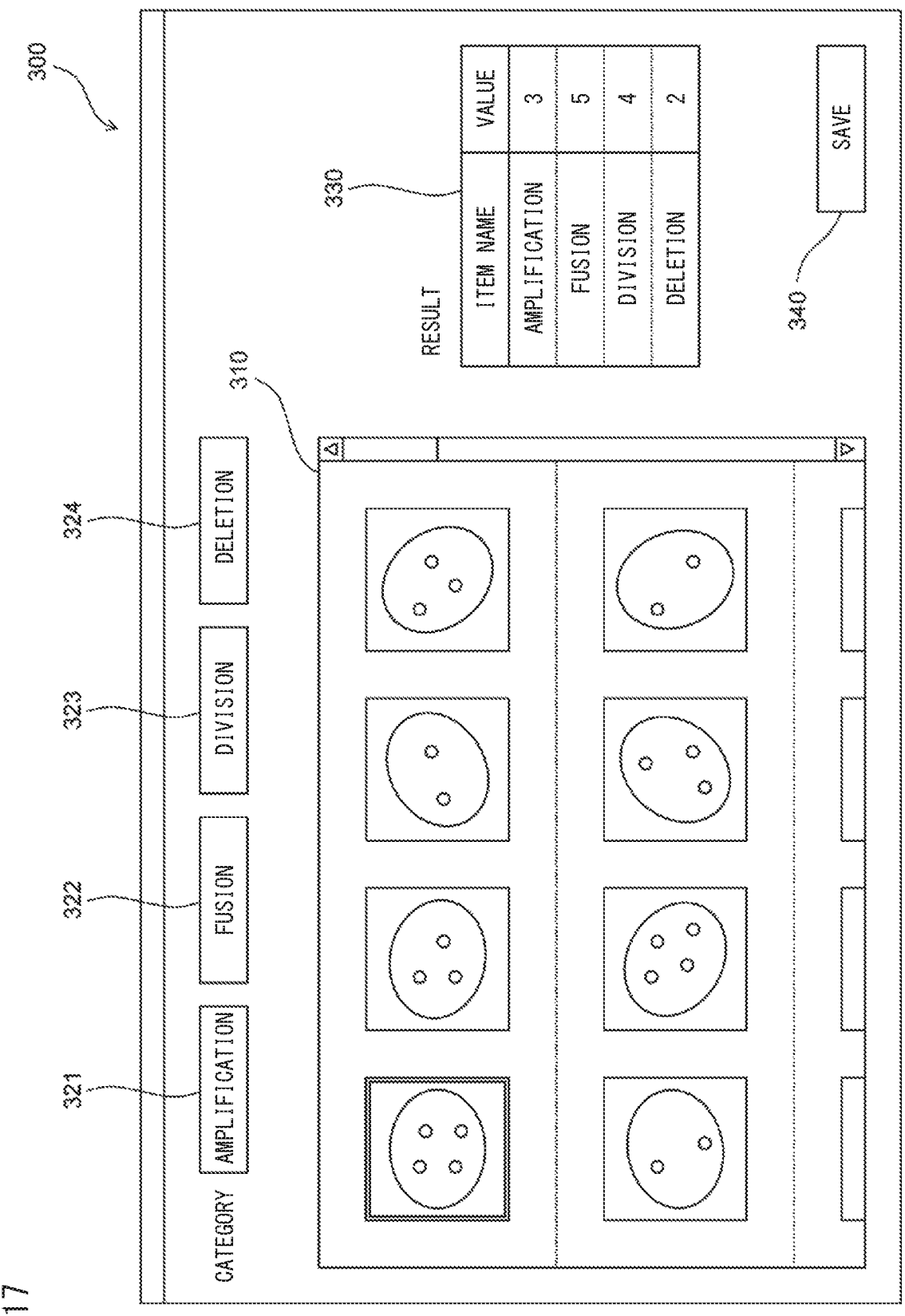
FIG. 17 shows a configuration of a visual observation result input screen for receiving a result of images classified on the basis of visual observation according to Embodiment 5.

As shown in FIG. 17, the visual observation result input screen 300 includes an image display region 310, buttons 321 to 324, a result display region 330, and a save button 340. Upon receiving an instruction to start visual observation input, the processing unit 11 causes the display unit 15 to display the visual observation result input screen 300 regarding the target sample.

The image display region 310 is obtained on the basis of the target sample, and shows images of the cells selected in step S105. The images in the image display region 310 are configured to be selectable. If an image is selected, this image is surrounded by a double line, as with the image on the up left in the image display region 310. The buttons 321 to 324 each receives a visual observation result of the image selected in the image display region 310. If the operator determines, by viewing the selected image, that gene amplification, gene fusion due to translocation, division due to translocation, or deletion has occurred in the cell shown in the image, the operator presses a corresponding one of the buttons 321 to 324 via the input unit 16. Accordingly, the value of the corresponding item in the result display region 330 is increased.

The result display region 330 shows, of all the cells included in the sample, the numbers of cells in which gene amplification, fusion, division, or deletion has occurred, respectively. That is, the result display region 330 shows the number of cells inputted by the operator via the buttons 321 to 324. When the save button 340 is pressed, the processing unit 11 stores, into the storage unit 11a, the result values shown in the result display region 330. In this manner, the operator can input the state of each cell by viewing the image, and can store the inputted result in the storage unit 11a. On the visual observation result input screen 300, only the cells that are stained well are selected and shown. Thus, the operator can efficiently determine the state of each cell by observing the image of the well-stained cell.

Embodiment 6

Embodiment 6 is obtained by applying the present disclosure to a cell selection apparatus configured to select cells.

Figure 18:
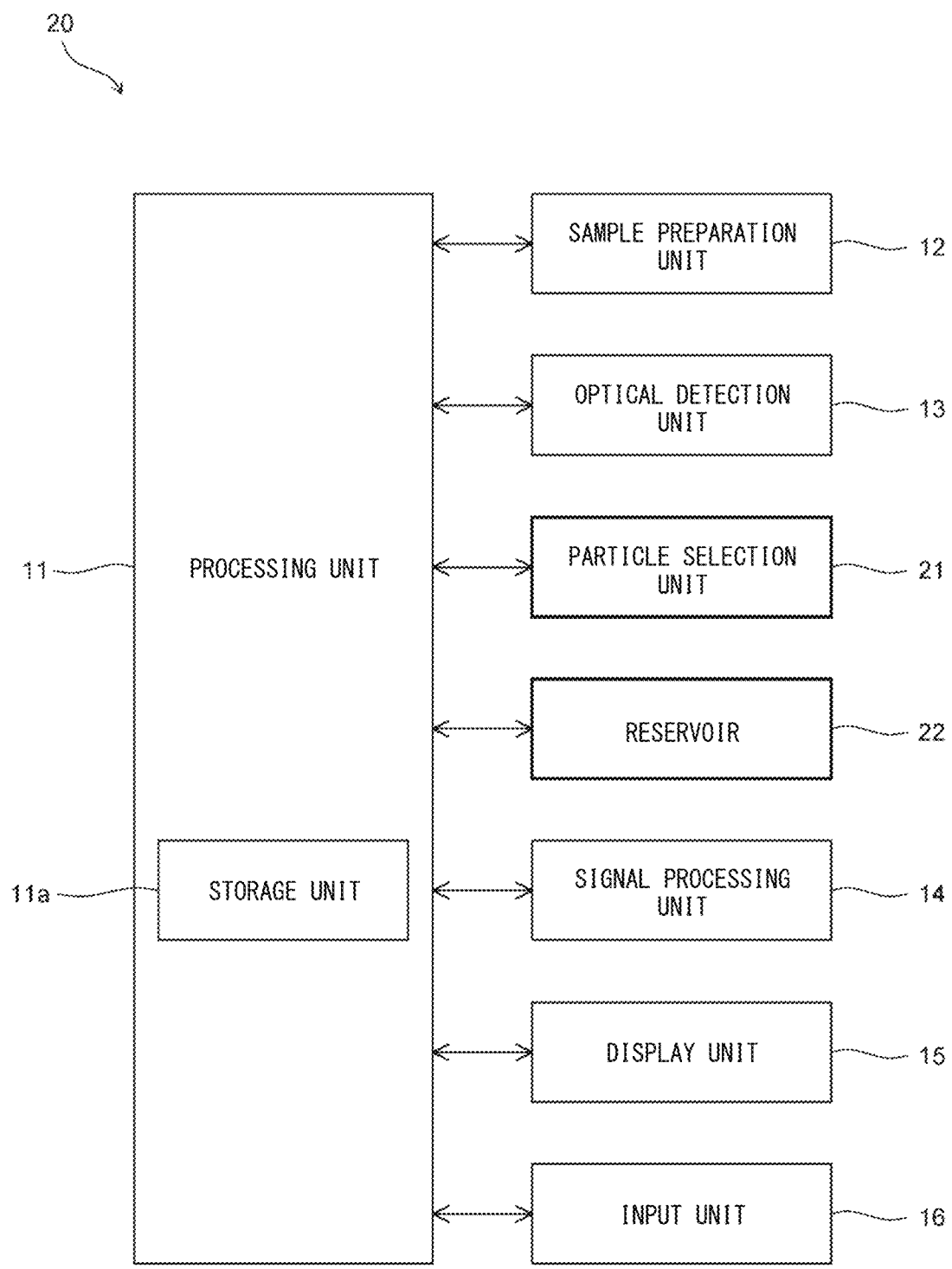
FIG. 18 is a block diagram showing a configuration of a cell selection apparatus according to Embodiment 6.
Figure 19:
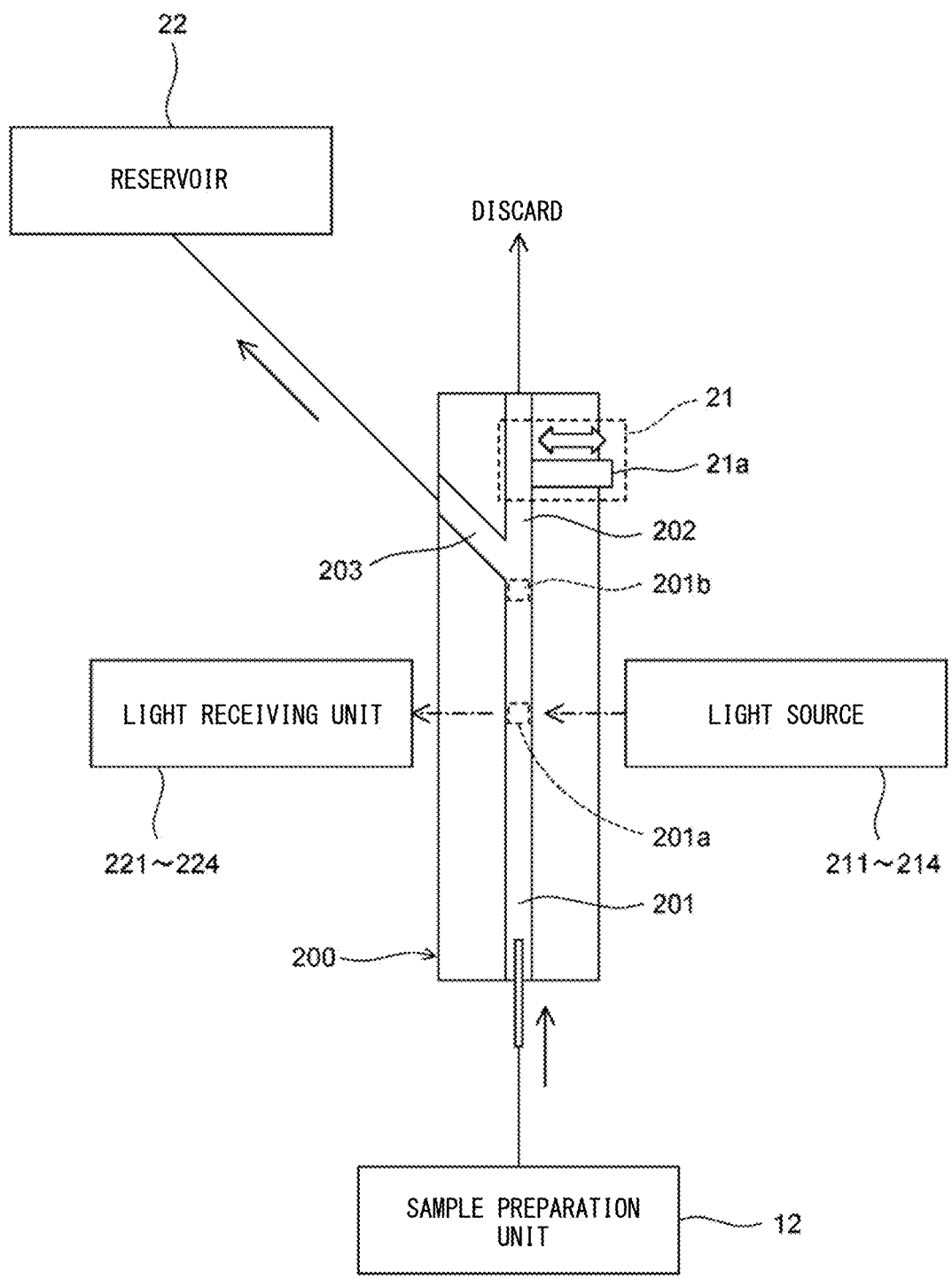
FIG. 19 is a schematic diagram showing a configuration of a particle selection unit, a reservoir, and a flow cell according to Embodiment 6.

As shown in FIG. 18, a cell selection apparatus 20 according to Embodiment 6 additionally has a particle selection unit 21 and a reservoir 22, compared with the cell detection apparatus 10 according to Embodiment 5. Other than this, as shown in FIG. 19, in Embodiment 6, the configuration of the flow cell 200 of the optical detection unit 13 is different from that of Embodiment 5. The other configurations of Embodiment 6 are the same as those of Embodiment 5.

As shown in FIG. 19, the flow cell 200 of Embodiment 6 has flow paths 202 and 203 formed therein, in addition to the flow path 201. The flow path 202 is formed on the extension line of the flow path 201. The flow path 203 is branched from the flow path 201, at a position between the flow paths 201 and 202. The flow path 202 is connected to a discard unit not shown. The flow path 203 is connected to the reservoir 22. The particle selection unit 21 is set at the flow path 202. The particle selection unit 21 includes a member 21a and a drive unit for projecting the member 21a into the flow path 202. When the member 21a is located at a position for opening the flow path 202, the sample flowing in the flow path 201 is not sent to the flow path 203, but is sent to the discard unit via the flow path 202. On the other hand, when the member 21a is located at a position for blocking the flow path 202, the sample flowing in the flow path 201 is not sent to the flow path 202, but is sent to the reservoir 22 via the flow path 203.

Figure 20:
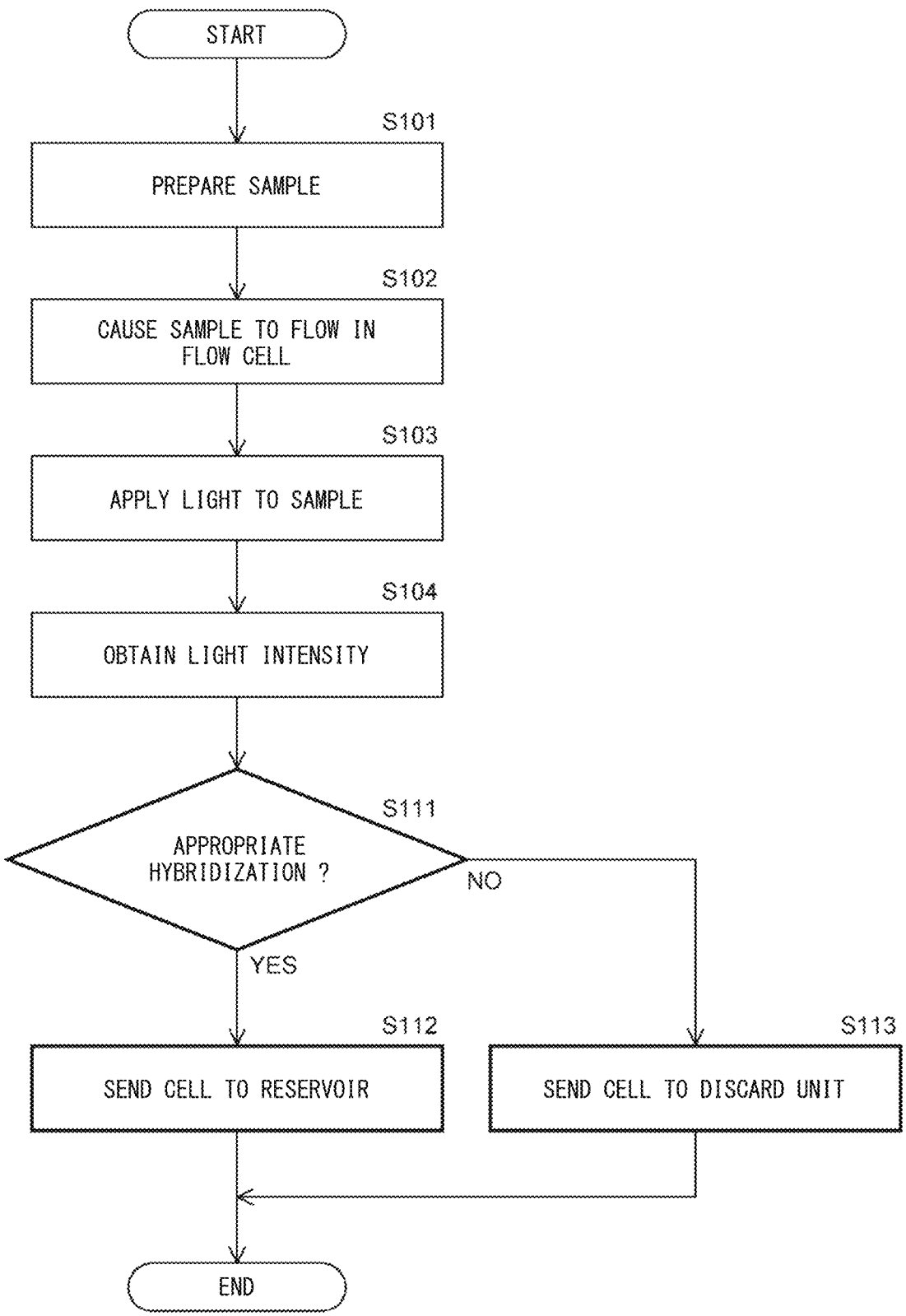
FIG. 20 is a flow chart showing an analysis target cell selection process to be performed by the cell selection apparatus according to Embodiment 6.

Next, with reference to FIG. 20, an analysis target cell selection process performed by the cell selection apparatus 20 will be described. The flow chart shown in FIG. 20 has step S111 to S113, instead of steps S105 and S106 in FIG. 16.

In step S101, as in Embodiment 5, the processing unit 11 causes a sample to be prepared. In step S102, the processing unit 11 drives the particle selection unit 21, to cause the flow path 202 to be open in advance, thereby causing the sample to flow from the sample preparation unit 12 to the flow path 201 of the flow cell 200. In step S103, as in Embodiment 5, the processing unit 11 causes lights to be applied to the sample. At this time, as shown in FIG. 19, the lights emitted from the light sources 211 to 214 are applied to the particle at a position 201a in the flow path 201, and the lights generated from the particle are received by the light receiving units 221 to 223 and the image capturing unit 224. In step S104, as in Embodiment 5, the processing unit 11 obtains the intensities of the fluorescences generated from the particle.

In step S111, on the basis of the intensities of the fluorescences having the wavelengths $\lambda 21$ and $\lambda 22$ generated from the particle at the position 201a, the processing unit 11 determines whether or not this particle is in the region 101 of the scattergram 100 shown in FIG. 4A. That is, with respect to the cell at the position 201a, the processing unit 11 determines whether or not appropriate hybridization has occurred, on the basis of the intensities of the intensity of the fluorescence from the fluorescent dye included in the evaluation probe, and the fluorescence from the nucleic acid staining dye.

If the processing unit 11 determines that appropriate hybridization has occurred with respect to the cell at the position 201a, the processing unit 11 drives, in step S112, the particle selection unit 21 to block the flow path 202 at the time when this cell is located at a position 201b in the flow path 201, thereby sending this cell to the reservoir 22. On the other hand, if the processing unit 11 determines that appropriate hybridization has occurred with respect to the cell at the position 201a, the processing unit 11 drives, in step S113, the particle selection unit 21 to open the flow path 202 at the time when this cell is located at the position 201b, thereby sending this cell to the discard unit.

According to Embodiment 6, a cell in which appropriate hybridization has occurred is selected as an analysis target, to be sent to the reservoir 22. Thus, for example, if abnormal cell detection is performed by the cell detection apparatus 10 or another detection apparatus by use of the cells held in the reservoir 22, accurate abnormal cell detection can be performed.

In Embodiment 6, in step S101, as in Embodiment 5, sample preparation is performed, with Her2 gene set as the detection target region and with Ch17 set as the evaluation target region. However, not limited thereto, sample preparation may be performed, with a combination of the detection target region and the evaluation target region set as in Embodiments 2 to 4. Also in this case, cells in which appropriate hybridization has occurred can be selected as the analysis target.

What is claimed is:
1. A cell selection method comprising:
a sample preparation step of preparing a sample by performing: staining of substantially an entirety of nucleic acid in each of cells by a first fluorescent dye; and hybridization with respect to an evaluation target region in DNA in each cell by an evaluation probe which comprises a second fluorescent dye;
a light receiving step of applying light to the sample and receiving fluorescence from the first fluorescent dye and fluorescence from the second fluorescent dye; and
a selection step of selecting an analysis target cell on the basis of intensity of the fluorescence from the first fluorescent dye and intensity of the fluorescence from the second fluorescent dye, wherein
the first fluorescent dye is a dye that emits fluorescence having a first wavelength,
the second fluorescent dye is a dye that emits fluorescence having a second wavelength different from the first wavelength, and
selecting as the analysis target cell a cell for which a proportion between the intensity of the fluorescence from the first fluorescent dye and the intensity of the fluorescence from the second fluorescent dye is evaluated as being in a predetermined range,
wherein the cells are human-derived cells,
wherein the hybridization forms a hydrogen bond between complementary nucleoside bases or complementary nucleotide bases, and
wherein the evaluation probe includes:
(i) a polynucleotide sequence complementary to a base sequence of the evaluation target region in DNA in the cell; and
(ii) a fluorescent substance.
2. The cell selection method of claim 1, wherein
in the light receiving step, light is applied to the sample flowing in a flow cell, and the fluorescence from the first fluorescent dye and the fluorescence from the second fluorescent dye are received.

3. The cell selection method of claim 1, wherein
in the light receiving step, light is applied to the sample disposed on a support, and the fluorescence from the first fluorescent dye and the fluorescence from the second fluorescent dye are received by means of a microscope.

4. The cell selection method of claim 1, wherein
the analysis target cell is selected for detecting genomic abnormality in the cell, and
the genomic abnormality is one of gene amplification, deletion, translocation, and inversion.

5. The cell selection method of claim 4, wherein
in a case of the genomic abnormality is gene amplification, the evaluation target region is, among DNA sequence regions in a nucleus of the cell, a part of a DNA sequence region excluding any DNA sequence region where amplification occurred due to the genomic abnormality, and
in a case of the genomic abnormality is deletion, the evaluation target region is, among DNA sequence regions in the nucleus of the cell, of a part of a DNA sequence region excluding any DNA sequence region where deletion occurred due to the genomic abnormality.

6. A cell selection method comprising:
a sample preparation step of preparing a sample by performing: staining of substantially an entirety of nucleic acid in each of cells by a first fluorescent dye; and hybridization with respect to an evaluation target region in DNA in each cell by an evaluation probe which comprises a second fluorescent dye;
an image capturing step of applying light to the sample and capturing an image of the cell in the sample;
determining, on the basis of the image of the cell captured in the image capturing step, brightness of an image of fluorescence from the first fluorescent dye and brightness of an image of fluorescence from the second fluorescent dye; and
selecting an analysis target cell on the basis of the brightness of the image of the fluorescence from the first fluorescent dye and the brightness of the image of the fluorescence from the second fluorescent dye, wherein a cell for which a proportion between the brightness of the image of the fluorescence from the first fluorescent dye and the brightness of the image of the fluorescence from the second fluorescent dye is evaluated as being in a predetermined range is selected as the analysis target cell, wherein
the first fluorescent dye is a dye that emits fluorescence having a first wavelength,
the second fluorescent dye is a dye that emits fluorescence having a second wavelength different from the first wavelength,
the cells are human-derived cells,
the hybridization forms a hydrogen bond between complementary nucleoside bases or complementary nucleotide bases, and
the evaluation probe includes:
(i) a polynucleotide sequence complementary to a base sequence of the evaluation target region in DNA in the cell; and
(ii) a fluorescent substance.

7. A cell detection method comprising:
a step of preparing a sample by performing: staining of substantially an entirety of nucleic acid in each of cells by a first fluorescent dye; hybridization with respect to an evaluation target region in DNA in each cell by an evaluation probe which comprises a second fluorescent dye; and hybridization with respect to a second target region in DNA in the cell by a detection probe which comprises a third fluorescent dye;
a step of applying light to the sample and receiving fluorescence from the first fluorescent dye, fluorescence from the second fluorescent dye, and fluorescence from the third fluorescent dye;
a step of selecting an analysis target cell on the basis of intensity of the fluorescence from the first fluorescent dye and intensity of the fluorescence from the second fluorescent dye, wherein a cell for which a proportion between the intensity of the fluorescence from the first fluorescent dye and the intensity of the fluorescence from the second fluorescent dye is evaluated as being in a predetermined range is selected as the analysis target cell; and
a step of identifying an abnormal cell from the analysis target cell on the basis of the fluorescence from the third fluorescent dye, wherein
the first fluorescent dye is a dye that emits fluorescence having a first wavelength,
the second fluorescent dye is a dye that emits fluorescence having a second wavelength different from the first wavelength,
the third fluorescent dye is a dye that emits fluorescence having a third wavelength different from the first and second wavelengths,
the cells are human-derived cells,
the hybridization forms a hydrogen bond between complementary nucleoside bases or complementary nucleotide bases, and
the evaluation probe includes:
(i) a polynucleotide sequence complementary to a base sequence of the evaluation target region in DNA in the cell; and
(ii) a fluorescent substance.

8. The cell detection method of claim 7, wherein
in the step of applying light to the sample, light is applied to the sample flowing in a flow cell, and the fluorescence from the first fluorescent dye, the fluorescence from the second fluorescent dye, and the fluorescence from the third fluorescent dye are received.

9. The cell detection method of claim 7, wherein
the abnormal cell is identified from the analysis target cell by comparing a ratio threshold with a ratio between intensity of the fluorescence from the third fluorescent dye and the intensity of the fluorescence from the second fluorescent dye.

10. The cell detection method of claim 9, wherein
a cell in which a value determined by dividing the intensity of the fluorescence from the third fluorescent dye by the intensity of the fluorescence from the second fluorescent dye exceeds Ra1 the ratio threshold is detected as the abnormal cell.

11. The cell detection method of claim 7, wherein
the second target region is, among DNA sequence regions in a nucleus of the cell, a DNA sequence region for detecting presence or absence of amplification caused by genomic abnormality,
the evaluation target region is, among DNA sequence regions in the nucleus of the cell, a part of a DNA sequence region excluding any DNA sequence region where amplification occurred due to genomic abnormality, and in the detection step, a cell in which amplification of a specific DNA sequence region has occurred is detected as the abnormal cell.

12. The cell detection method of claim 11, wherein
the second target region is Her2 gene,
the evaluation target region is a part of a DNA sequence region excluding the Her2 gene in chromosome 17, and
in the detection step, a cell in which the Her2 gene has been amplified is detected as the abnormal cell.

13. The cell detection method of claim 7, wherein
the second target region is, among DNA sequence regions in a nucleus of the cell, a DNA sequence region for determining presence or absence of translocation at least in part on the basis of at least one of cut points or fusion points, and
in the detection step, a cell in which translocation has occurred is detected as the abnormal cell.

14. The cell detection method of claim 13, wherein
a combination of the second target region and the evaluation target region is BCR gene and ABL gene, and
in the detection step, a cell in which the BCR gene and the ABL gene have been translocated to form a BCR-ABL fusion gene is detected as the abnormal cell.

* * * * *